(12) United States Patent
Yamamoto et al.

(10) Patent No.: US 8,216,768 B2
(45) Date of Patent: Jul. 10, 2012

(54) PHOTOACID GENERATOR AND PHOTOREACTIVE COMPOSITION

(75) Inventors: Katsumasa Yamamoto, Hyogo (JP); Hirofumi Yamaguchi, Hyogo (JP); Michio Suzuki, Hyogo (JP)

(73) Assignee: Sumitomo Seika Chemicals Co., Ltd., Kako-gun (JP)

( * ) Notice: Subject to any disclaimer, the term of this patent is extended or adjusted under 35 U.S.C. 154(b) by 183 days.

(21) Appl. No.: 12/741,325

(22) PCT Filed: Oct. 30, 2008

(86) PCT No.: PCT/JP2008/069783
§ 371 (c)(1),
(2), (4) Date: May 13, 2010

(87) PCT Pub. No.: WO2009/069428
PCT Pub. Date: Jun. 4, 2009

(65) Prior Publication Data
US 2010/0233621 A1    Sep. 16, 2010

(30) Foreign Application Priority Data

Nov. 28, 2007  (JP) .................. 2007-307632
Nov. 28, 2007  (JP) .................. 2007-307633
Nov. 28, 2007  (JP) .................. 2007-307634

(51) Int. Cl.
G03F 7/004    (2006.01)
G03F 7/028    (2006.01)
C07D 409/12   (2006.01)

(52) U.S. Cl. ............. 430/270.1; 430/913; 430/914; 549/59

(58) Field of Classification Search .......... 430/270.1, 430/913, 914; 549/59
See application file for complete search history.

(56) References Cited

U.S. PATENT DOCUMENTS

| | | | |
|---|---|---|---|
| 3,205,157 A | 9/1965 | Licari et al. | |
| 4,231,951 A | 11/1980 | Smith et al. | |
| 4,239,897 A * | 12/1980 | Rossy et al. | 549/61 |
| 4,242,518 A * | 12/1980 | Rossy et al. | 549/61 |
| 5,731,364 A | 3/1998 | Sinta et al. | |
| 6,696,216 B2 | 2/2004 | Li et al. | |
| 2003/0008230 A1 | 1/2003 | Li et al. | |

FOREIGN PATENT DOCUMENTS

| | | | |
|---|---|---|---|
| JP | 2004-189720 A | 7/2004 | |
| JP | 2005-504329 A | 2/2005 | |
| JP | 2008273878 A * | 11/2008 | |
| JP | 2011195548 A * | 10/2011 | |

OTHER PUBLICATIONS

Notification of Transmittal of Translation of the International Preliminary Report on Patentability (Form PCT/IB/338) of International Application No. PCT/JP2008/069783 mailed Jun. 17, 2010 with Forms PCT/IB/373, PCT/ISA/237 and PCT/IB/326.
J. Cameron et al, "Complex Triarylsulfonium Salts as Photoacid Generators for Deep UV Microlithography: Synthesis, Identified and Lithographic Characterization of key Individual Components", SPIE, vol. 3049, pp. 473-484.
International Search Report of PCT/JP2008/069783, date of mailing Jan. 13, 2009.
Supplementary European Search Report mailed on Jan. 17, 2012, issued in corresponding European Patent Application No. 08854014.1.

\* cited by examiner

*Primary Examiner* — Amanda C. Walke
(74) *Attorney, Agent, or Firm* — Westerman, Hattori, Daniels & Adrian, LLP

(57) ABSTRACT

A photoacid generator, which shows very high sensitivity in the near ultraviolet range of about 300 to 400 nm, and also can remarkably increase a reaction rate of a photoreactive composition using the same, and a photoreactive composition which can initiate the reaction even by irradiation with near ultraviolet light within a short time and also can obtain a desired reaction product. A dithienyl sulfide disulfonium salt represented by the formula (A1):

(A1)

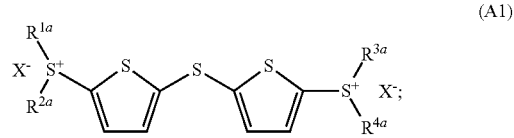

a dithienyl sulfide sulfonium salt represented by the formula (B1):

(B1)

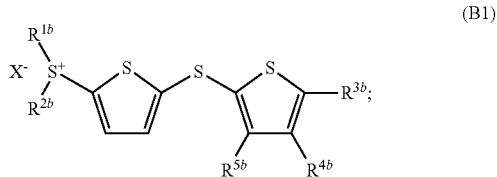

and a phenylthiothiophene sulfonium salt represented by the formula (C1):

(C1)

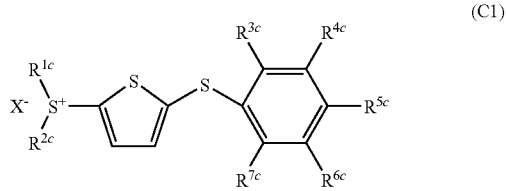

9 Claims, No Drawings

US 8,216,768 B2

PHOTOACID GENERATOR AND PHOTOREACTIVE COMPOSITION

TECHNICAL FIELD

The present invention relates to a compound, a photoacid generator containing the (5-arylthio-thiophen-2-yl)-diaryl sulfonium salt, and a photoreactive composition containing the photoacid generator.

Specific examples of the (5-arylthio-thiophen-2-yl)-diaryl sulfonium salt of the present invention include a dithienyl sulfide disulfonium salt, a dithienyl sulfide sulfonium salt and a phenylthiothiophene sulfonium salt A first aspect of the present invention relates to a dithienyl sulfide disulfonium salt as a novel compound, a photoacid generator containing the dithienyl sulfide disulfonium salt, and a photoreactive composition containing the photoacid generator.

A second aspect of the present invention relates to a dithienyl sulfide sulfonium salt as a novel compound, a photoacid generator containing the dithienyl sulfide sulfonium salt, and a photoreactive composition containing the photoacid generator.

A third aspect of the present invention relates to a phenylthiothiophene sulfonium salt as a novel compound, a photoacid generator containing the phenylthiothiophene sulfonium salt, and a photoreactive composition containing the photoacid generator.

BACKGROUND ART

Since it is simple to handle a photoreactive composition, the photoreactive composition is widely used for printing plate materials, various resists and ultraviolet curable coating materials.

As the photoreactive composition, a composition of a photopolymerizable monomer and/or a photopolymerizable polymer and an aryl diazonium salt (see Patent Document 1) and a photoreactive composition containing a photoacid generator such as a triaryl sulfonium complex salt added therein (see Patent Document 2) have hitherto been known.

However, when these photoacid generators such as an aryl diazonium salt and a triaryl sulfonium complex salt are used, since the maximum absorption wavelength is 300 nm or less, there was a problem that a reaction rate of the photoreactive composition is insufficient under the conditions where a light source in the near ultraviolet range of about 300 to 400 nm is used.

The present inventors have intensively studied so as to solve such a problem of the prior art and fond that a specific compound shows high sensitivity in the near ultraviolet range, thus proposing a photopolymerization initiator using the compound and a photocurable composition containing the same (see Patent Document 3).

Patent Document 1: Specification of U.S. Pat. No. 3,205,157
Patent Document 2: Specification of U.S. Pat. No. 4,231,951
Patent Document 3: Japanese Unexamined Patent Publication (Kokai) No. 2004-189720

DISCLOSURE OF THE INVENTION

Problems to be Solved by the Invention

With recent diversification of use of photoacid generators and photoreactive compositions, various photoacid generators have been required to cope with the diversification of use. Especially, it is required to propose a photoacid generator which shows very high sensitivity in the near ultraviolet range, and can initiate and complete the reaction of a photoreactive composition by light irradiation using various near ultraviolet light sources within a short time.

An object of the present invention is to provide a photoacid generator which can meet these requirements and shows very high sensitivity in the near ultraviolet range of about 300 to 400 nm, and also can remarkably increase a reaction rate of a photoreactive composition using the same, and to provide a photoreactive composition which can initiate the reaction even by irradiation with near ultraviolet light within a short time and also can obtain a desired reaction product.

Means for Solving the Problems

The present invention relates to a (5-arylthio-thiophen-2-yl)-diaryl sulfonium salt represented by the general formula:

[Chemical Formula 1]

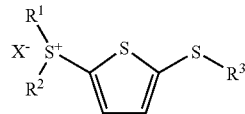

wherein $R^1$ and $R^2$ each independently represents an optionally substituted monocyclic carbon ring group, an optionally substituted condensed polycyclic carbon ring group or an optionally substituted monocyclic heterocyclic group, $R^3$ represents an optionally substituted aryl group, and $X^-$ represents an inorganic acid ion or an organic acid ion; a photoacid generator containing the (5-arylthio-thiophen-2-yl)-diaryl sulfonium salt; and a photoreactive composition containing the photoacid generator.

A first aspect of the present invention relates to a dithienyl sulfide disulfonium salt represented by the formula (A1):

[Chemical Formula 2]

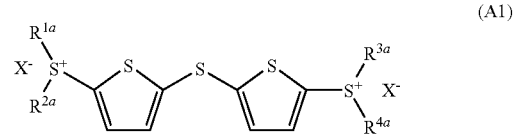

wherein $R^{1a}$ to $R^{4a}$ each independently represents an optionally substituted monocyclic carbon ring group, an optionally substituted condensed polycyclic carbon ring group or an optionally substituted monocyclic heterocyclic group, and $X^-$ represents an inorganic acid ion or an organic acid ion; a photoacid generator containing the dithienyl sulfide disulfonium salt; and a photoreactive composition containing the photoacid generator and an acid reactive compound.

A second aspect of the present invention relates to a dithienyl sulfide sulfonium salt represented by the formula (B1):

[Chemical Formula 3]

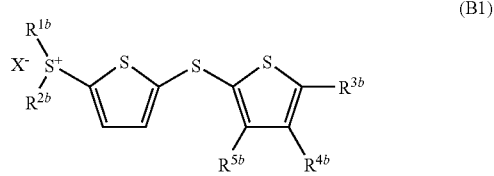

wherein $R^{1b}$ and $R^{2b}$ each independently represents an optionally substituted monocyclic carbon ring group, an optionally substituted condensed polycyclic carbon ring group or an optionally substituted monocyclic heterocyclic group, $R^{3b}$ to $R^{5b}$ each independently represents a hydrogen atom, an alkyl group having 1 to 10 carbon atoms, an alkoxy group having 1 to 4 carbon atoms, an acyl group or a hydroxyl group, and $X^-$ represents an inorganic acid ion or an organic acid ion; a photoacid generator containing the dithienyl sulfide sulfonium salt; and a photoreactive composition containing the photoacid generator and an acid reactive compound.

A third aspect of the present invention relates to a phenylthiothiophene sulfonium salt represented by the formula (C1):

[Chemical Formula 4]

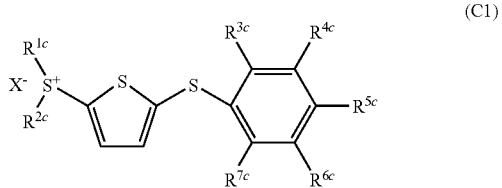

(C1)

wherein $R^{1c}$ and $R^{2c}$ each independently represents an optionally substituted monocyclic carbon ring group, an optionally substituted condensed polycyclic carbon ring group or an optionally substituted monocyclic heterocyclic group, $R^{3c}$ to $R^{7c}$ each independently represents a hydrogen atom, an alkyl group having 1 to 10 carbon atoms, an alkoxy group having 1 to 4 carbon atoms, an acyl group or a hydroxyl group, and $X^-$ represents an inorganic acid ion or an organic acid ion; a photoacid generator containing the phenylthiothiophene sulfonium salt; and a photoreactive composition containing the photoacid generator and an acid reactive compound.

Effects of the Invention

By using a photoacid generator containing the dithienyl sulfide disulfonium salt according to the first aspect of the present invention, it is possible to provide a photoreactive composition which can initiate the reaction even by irradiation with near ultraviolet within a short time and also can obtain a desired reaction product.

By using a photoacid generator containing the dithienyl sulfide sulfonium salt according to the second aspect of the present invention, it is possible to provide a photoreactive composition which can initiate the reaction even by irradiation with near ultraviolet within a short time and also can obtain a desired reaction product.

By using a photoacid generator containing the phenylthiothiophene sulfonium salt according to the third aspect of the present invention, it is possible to provide a photoreactive composition which can initiate the reaction even by irradiation with near ultraviolet within a short time and also can obtain a desired reaction product.

Aspects of the Invention

The dithienyl sulfide disulfonium salt according to the first aspect of the present invention is a compound represented by the following formula (A1).

[Chemical Formula 5]

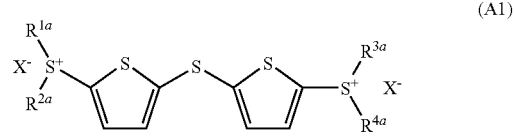

(A1)

In the formula (A1), $R^{1a}$ to $R^{4a}$ each independently represents an optionally substituted monocyclic carbon ring group, an optionally substituted condensed polycyclic carbon ring group or an optionally substituted monocyclic heterocyclic group, and $X^-$ represents an inorganic acid ion or an organic acid ion.

Examples of the optionally substituted monocyclic carbon ring group represented by $R^{1a}$ to $R^{4a}$ include a phenyl group and a phenyl group having a substituent.

Examples of the optionally substituted condensed polycyclic carbon ring group include a naphthyl group and a naphthyl group having a substituent.

Examples of the optionally substituted monocyclic heterocyclic group include a thienyl group and a thienyl group having a substituent.

Examples of the substituent include a hydroxyl group, an acetoxy group, a phenyl group, an alkyl group having 1 to 10 carbon atoms, an alkoxy group having 1 to 4 carbon atoms, an alkylthio group having 1 to 4 carbon atoms, and a halogen atom.

Examples of the alkyl group having 1 to 10 carbon atoms include a methyl group, an ethyl group, a propyl group, a butyl group, a pentyl group, a hexyl group, an octyl group, and a decyl group.

Examples of the alkoxy group having 1 to 4 carbon atoms include a methoxy group, an ethoxy group, a propoxy group, a butoxy group, and a methoxyethoxy group.

Examples of the alkylthio group having 1 to 4 carbon atoms include a methylthio group, an ethylthio group, a propylthio group, and a butylthio group.

Examples of the halogen atom include a fluorine atom, a chlorine atom, a bromine atom, and an iodine atom.

As the group represented $R^{1a}$ to $R^{4a}$ in the formula (A1), an optionally substituted monocyclic carbon ring group is preferably used, and a phenyl group, and a phenyl group having a substituent is more preferably used. As the substituent in the phenyl group having a substituent, a methyl group, an ethyl group, an n-propyl group, an isopropyl group, an n-butyl group, a tert-butyl group, a methoxy group, an ethoxy group, an n-propoxy group, an isopropoxy group, an n-butoxy group, an isobutoxy group, a sec-butoxy group, a tert-butoxy group, a methylthio group and a fluorine atom are preferably used, and a methyl group, an ethyl group, an n-propyl group, an isopropyl group, an n-butyl group, a methoxy group, an ethoxy group, an n-propoxy group, an isopropoxy group, and an n-butoxy group are more preferably used.

The optionally substituted monocyclic carbon ring group, the optionally substituted condensed polycyclic carbon ring group and the optionally substituted monocyclic heterocyclic group may have one substituent or may have a plurality of substituents. In the case of having a plurality of substituents, the substituent may be the same or different.

Examples of the inorganic acid ion represented by $X^-$ in the formula (A1) include, but are not particularly limited to, a hexafluoroantimonic acid ion, a hexafluoroarsenic acid ion, a hexafluorophosphoric acid ion, a pentafluorohydroxoantimonic acid ion, a tetrafluoroboric acid ion, a tetrakis(pentafluorophenyl)boric acid ion, a tetrakis(trifluoromethylphenyl)boric acid ion, a trifluoro(pentafluorophenyl)boric acid ion, a tetrakis(difluorophenyl)boric acid ion, and a difluorobis(pentafluorophenyl)boric acid ion.

Examples of the organic acid ion represented by $X^-$ in the formula (A1) include, but are not particularly limited to, a methanesulfonic acid ion, an ethanesulfonic acid ion, a propanesulfonic acid ion, a butanesulfonic acid ion, an octanesulfonic acid ion, a trifluoromethanesulfonic acid ion, a perfluorobutanesulfonic acid ion, a perfluorohexanesulfonic acid ion, a benzenesulfonic acid ion, a benzene-1,3-disulfonic acid ion, a p-toluenesulfonic acid ion, an anthraquinone-l-sulfonic acid ion, an anthraquinone-2-sulfonic acid ion, an anthraquinone-1,5-disulfonic acid ion, a methanecarboxylic acid ion, an ethanecarboxylic acid ion, a propanecarboxylic acid ion, a butanecarboxylic acid ion, an octanecarboxylic acid ion, a trifluoromethanecarboxylic acid ion, a benzenecarboxylic acid ion, a p-toluenecarboxylic acid ion, a bis(trifluoromethanesulfonyl)imide ion, and a tris(trifluoromethanesulfonyl)methide ion.

Of these acid ions, a hexafluorophosphoric acid ion, a tetrakis(pentafluorophenyl)boric acid ion, a trifluoromethanesulfonic acid ion, and a perfluorobutanesulfonic acid ion are preferably used in view of acid strength and safety of an acid generated when the dithienyl sulfide disulfonium salt is used as the photoacid generator.

Specific examples of the dithienyl sulfide disulfonium salt according to the first aspect of the present invention include: (thiodi-5,2-thienylene)bis(bisphenylsulfonium) bisperfluorobutanesulfonate, (thiodi-5,2-thienylene)bis(bisphenylsulfonium) bistrifluoromethanesulfonate, (thiodi-5,2-thienylene)bis(bisphenylsulfonium)bishexafluorophosphate, (thiodi-5,2-thienylene)bis(bisphenylsulfonium)bis[tetrakis(pentafluorophenyl)borate], (thiodi-5,2-thienylene)bis[bis(4-methylphenyl)sulfonium]bisperfluorobutanesulfonate, (thiodi-5,2-thienylene)bis[bis(4-methylphenyl)sulfonium]bistrifluoromethanesulfonate, (thiodi-5,2-thienylene)bis[bis(4-methylphenyl)sulfonium]bishexafluorophosphate, (thiodi-5,2-thienylene)bis[bis(4-methylphenyl)sulfonium]bis[tetrakis(pentafluorophenyl)borate], (thiodi-5,2-thienylene)bis[bis(4-ethylphenyl)sulfonium]bisperfluorobutanesulfonate, (thiodi-5,2-thienylene)bis[bis(4-ethylphenyl)sulfonium]bistrifluoromethanesulfonate, (thiodi-5,2-thienylene)bis[bis(4-ethylphenyl)sulfonium]bishexafluorophosphate, (thiodi-5,2-thienylene)bis[bis(4-ethylphenyl)sulfonium]bis[tetrakis(pentafluorophenyl)borate], (thiodi-5,2-thienylene)bis[bis(4-n-propylphenyl)sulfonium]bisperfluorobutanesulfonate, (thiodi-5,2-thienylene)bis[bis(4-n-propylphenyl)sulfonium]bistrifluoromethanesulfonate, (thiodi-5,2-thienylene)bis[bis(4-n-propylphenyl)sulfonium]bishexafluorophosphate, (thiodi-5,2-thienylene)bis[bis(4-n-propylphenyl)sulfonium]bis[tetrakis(pentafluorophenyl)borate], (thiodi-5,2-thienylene)bis[bis(4-isopropylphenyl)sulfonium]bisperfluorobutanesulfonate, (thiodi-5,2-thienylene)bis[bis(4-isopropylphenyl)sulfonium]bistrifluoromethanesulfonate, (thiodi-5,2-thienylene)bis[bis(4-isopropylphenyl)sulfonium]bishexafluorophosphate, (thiodi-5,2-thienylene)bis[bis(4-isopropylphenyl)sulfonium]bis[tetrakis(pentafluorophenyl)borate], (thiodi-5,2-thienylene)bis[bis(4-n-butylphenyl)sulfonium]bisperfluorobutanesulfonate, (thiodi-5,2-thienylene)bis[bis(4-n-butylphenyl)sulfonium]bistrifluoromethanesulfonate, (thiodi-5,2-thienylene)bis[bis(4-n-butylphenyl)sulfonium]bishexafluorophosphate, (thiodi-5,2-thienylene)bis[bis(4-n-butylphenyl)sulfonium]bis[tetrakis(pentafluorophenyl)borate], (thiodi-5,2-thienylene)bis[bis(4-tert-butylphenyl)sulfonium]bisperfluorobutanesulfonate, (thiodi-5,2-thienylene)bis[bis(4-tert-butylphenyl)sulfonium]bistrifluoromethanesulfonate, (thiodi-5,2-thienylene)bis[bis(4-tert-butylphenyl)sulfonium]bishexafluorophosphate, (thiodi-5,2-thienylene)bis[bis(4-tert-butylphenyl)sulfonium]bis[tetrakis(pentafluorophenyl)borate], (thiodi-5,2-thienylene)bis[bis(4-methoxyphenyl)sulfonium]bisperfluorobutanesulfonate, (thiodi-5,2-thienylene)bis[bis(4-methoxyphenyl)sulfonium]bistrifluoromethanesulfonate, (thiodi-5,2-thienylene)bis[bis(4-methoxyphenyl)sulfonium]bishexafluorophosphate, (thiodi-5,2-thienylene)bis[bis(4-methoxyphenyl)sulfonium]bis[tetrakis(pentafluorophenyl)borate], (thiodi-5,2-thienylene)bis[bis(4-ethoxyphenyl)sulfonium]bisperfluorobutanesulfonate, (thiodi-5,2-thienylene)bis[bis(4-ethoxyphenyl)sulfonium]bistrifluoromethanesulfonate, (thiodi-5,2-thienylene)bis[bis(4-ethoxyphenyl)sulfonium]bishexafluorophosphate, (thiodi-5,2-thienylene)bis[bis(4-ethoxyphenyl)sulfonium]bis[tetrakis(pentafluorophenyl)borate], (thiodi-5,2-thienylene)bis[bis(4-n-propoxyphenyl)sulfonium]bisperfluorobutanesulfonate, (thiodi-5,2-thienylene)bis[bis(4-n-propoxyphenyl)sulfonium]bistrifluoromethanesulfonate, (thiodi-5,2-thienylene)bis[bis(4-n-propoxyphenyl)sulfonium]bishexafluorophosphate, (thiodi-5,2-thienylene)bis[bis(4-n-propoxyphenyl)sulfonium]bis[tetrakis(pentafluorophenyl)borate], (thiodi-5,2-thienylene)bis[bis(4-isopropoxyphenyl)sulfonium]bisperfluorobutanesulfonate, (thiodi-5,2-thienylene)bis[bis(4-isopropoxyphenyl)sulfonium]bistrifluoromethanesulfonate, (thiodi-5,2-thienylene)bis[bis(4-isopropoxyphenyl)sulfonium]bishexafluorophosphate, (thiodi-5,2-thienylene)bis[bis(4-isopropoxyphenyl)sulfonium]bis[tetrakis(pentafluorophenyl)borate], (thiodi-5,2-thienylene)bis[bis(4-n-butoxyphenyl)sulfonium]bisperfluorobutanesulfonate, (thiodi-5,2-thienylene)bis[bis(4-n-butoxyphenyl)sulfonium]bistrifluoromethanesulfonate, (thiodi-5,2-thienylene)bis[bis(4-n-butoxyphenyl)sulfonium]bishexafluorophosphate, (thiodi-5,2-thienylene)bis[bis(4-n-butoxyphenyl)sulfonium]bis[tetrakis(pentafluorophenyl)borate], (thiodi-5,2-thienylene)bis[bis(4-isobutoxyphenyl)sulfonium]bisperfluorobutanesulfonate, (thiodi-5,2-thienylene)bis[bis(4-isobutoxyphenyl)sulfonium]bistrifluoromethanesulfonate, (thiodi-5,2-thienylene)bis[bis(4-isobutoxyphenyl)sulfonium]bishexafluorophosphate, (thiodi-5,2-thienylene)bis[bis(4-isobutoxyphenyl)sulfonium]bis[tetrakis(pentafluorophenyl)borate], (thiodi-5,2-thienylene)bis[bis(4-sec-butoxyphenyl)sulfonium]bisperfluorobutanesulfonate, (thiodi-5,2-thienylene)bis[bis(4-sec-butoxyphenyl)sulfonium]bistrifluoromethanesulfonate, (thiodi-5,2-thienylene)bis[bis(4-sec-butoxyphenyl)sulfonium]bishexafluorophosphate, (thiodi-5,2-thienylene)bis[bis(4-sec-butoxyphenyl)sulfonium]bis[tetrakis(pentafluorophenyl)borate], (thiodi-5,2-thienylene)bis[bis(4-tert-butoxyphenyl)sulfonium]bisperfluorobutanesulfonate, (thiodi-5,2-thienylene)bis[bis(4-tert-butoxyphenyl)sulfonium]bistrifluoromethanesulfonate, (thiodi-5,2-thienylene)bis[bis(4-tert-butoxyphenyl)sulfonium]bishexafluorophosphate, (thiodi-5,2-thienylene)bis[bis(4-tert-butoxyphenyl)sulfonium]bis[tetrakis(pentafluorophenyl)borate], (thiodi-5,2-thienylene)bis[bis(4-methylthiophenyl)sulfonium]bisperfluorobutanesulfonate, (thiodi-5,2-thienylene)bis[bis(4-methylthiophenyl)sulfonium]bistrifluoromethanesulfonate, (thiodi-5,2-thienylene)bis[bis(4-methylthiophenyl)sulfonium]bishexafluorophosphate, (thiodi-5,2-thienylene)bis[bis(4-methylthiophenyl)sulfonium]bis[tetrakis(pentafluorophenyl)borate], (thiodi-5,2-thienylene)bis[bis(4-fluorophenyl)sulfonium]bisperfluorobutanesulfonate, (thiodi-5,2-thienylene)bis[bis(4-fluorophenyl)sulfonium]

bistrifluoromethanesulfonate, (thiodi-5,2-thienylene)bis[bis (4-fluorophenyl)sulfonium]bishexafluorophosphate, (thiodi-5,2-thienylene)bis[bis(4-fluorophenyl)sulfonium]bis [tetrakis(pentafluorophenyl)borate], [[2-(di(4-methylphenyl)sulfonio)thiophen-5-yl]-thio-thiophen-5-yl]di (4-methoxyphenyl)sulfonium)bisperfluorobutanesulfonate, [[2-(di(4-methylphenyl)sulfonio)thiophen-5-yl]-thio-thiophen-5-yl](di(4-methoxyphenyl)sulfonium) bistrifluoromethanesulfonate, [[2-(di(4-methylphenyl)sulfonio) thiophen-5-yl]-thio-thiophen-5-yl]di(4-methoxyphenyl) sulfonium)bishexafluorophosphate, [[2-(di(4-methylphenyl) sulfonio)thiophen-5-yl]-thio-thiophen-5-yl]di(4-methoxyphenyl)sulfonium) bis[tetrakis(pentafluorophenyl) borate], (thiodi-5,2-thienylene)bis(dithienylsulfonium) bisperfluorobutanesulfonate, (thiodi-5,2-thienylene)bis (dithienylsulfonium)bistrifluoromethanesulfonate, (thiodi-5, 2-thienylene)bis(dithienylsulfonium) bishexafluorophosphate, (thiodi-5,2-thienylene)bis(dithienylsulfonium) bis [tetrakis(pentafluorophenyl)borate], (thiodi-5,2-thienylene) bis[bis(2-naphthyl)sulfonium]bisperfluorobutanesulfonate, (thiodi-5,2-thienylene)bis[bis(2-naphthyl)sulfonium]bistrifluoromethanesulfonate, (thiodi-5,2-thienylene)bis[bis(2-naphthyl)sulfonium]bishexafluorophosphate, and (thiodi-5, 2-thienylene)bis[bis(2-naphthyl)sulfonium]bis[tetrakis (pentafluorophenyl)borate].

The dithienyl sulfide disulfonium salt represented by the formula (A1) can be produced, for example, by a method of condensing sulfoxide represented by the following formula (A2):

[Chemical Formula 6]

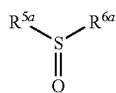

(A2)

wherein $R^{5a}$ and $R^{6a}$ each represents a group represented by any one of $R^{1a}$ to $R^{4a}$ in the formula (A1), with 2,2'-dithienyl sulfide in the presence of a condensing agent and a strong acid, and reacting the condensation reaction product with an alkali metal salt of an inorganic acid corresponding to the inorganic acid ion, or an alkali metal salt of an organic acid corresponding to the organic acid ion.

Specific examples of the sulfoxide represented by the formula (A2) include diphenyl sulfoxide, bis(4-methylphenyl) sulfoxide, bis(4-ethylphenyl) sulfoxide, bis(4-n-propylphenyl) sulfoxide, bis(4-isopropylphenyl) sulfoxide, bis(4-n-butylphenyl) sulfoxide, bis(4-tert-butylphenyl)sulfoxide, bis (4-phenylphenyl)sulfoxide, bis(4-methoxyphenyl)sulfoxide, bis(4-ethoxyphenyl)sulfoxide, bis(4-n-propoxyphenyl)sulfoxide, bis(4-isopropoxyphenyl)sulfoxide, bis(4-n-butoxyphenyl)sulfoxide, bis(4-isobutoxyphenyl)sulfoxide, bis(4-sec-butoxyphenyl)sulfoxide, bis(4-tert-butoxyphenyl) sulfoxide, bis(4-methylthiophenyl)sulfoxide, bis(4-ethylthiophenyl)sulfoxide, bis(4-n-propylthiophenyl) sulfoxide, bis(4-isopropylthiophenyl)sulfoxide, bis(4-n-butylthiophenyl)sulfoxide, bis(4-tert-butylthiophenyl) sulfoxide, bis(4-hydroxyphenyl)sulfoxide, bis(4-acetoxyphenyl)sulfoxide, bis(4-fluorophenyl)sulfoxide, bis (4-chlorophenyl)sulfoxide, bis(4-bromophenyl)sulfoxide, bis(4-iodophenyl)sulfoxide, bis(2,4-dimethylphenyl)sulfoxide, bis(3,4-dimethylphenyl)sulfoxide, bis(2,4,6-trimethylphenyl)sulfoxide, di-(2-thienyl)sulfoxide, and di-(2-naphthyl)sulfoxide.

Of these sulfoxides, diphenyl sulfoxide, bis(4-methylphenyl)sulfoxide, bis(4-ethylphenyl)sulfoxide, bis(4-n-propylphenyl)sulfoxide, bis(4-isopropylphenyl)sulfoxide, bis(4-n-butylphenyl)sulfoxide, bis(4-methoxyphenyl)sulfoxide, bis (4-ethoxyphenyl)sulfoxide, bis(4-n-propoxyphenyl) sulfoxide, bis(4-isopropoxyphenyl)sulfoxide, bis(4-n-butoxyphenyl)sulfoxide, bis(4-methylthiophenyl)sulfoxide, bis(4-fluorophenyl)sulfoxide, and bis(2,4-dimethylphenyl) sulfoxide are preferably used.

In the reaction of condensing sulfoxide with 2,2'-dithienyl sulfide in the presence of a condensing agent and a strong acid, sulfoxides may be used alone, or two or more kinds thereof may be used in combination. When sulfoxides are used alone, symmetrical dithienyl sulfide disulfonium salts in the formula (A1) can be produced. When two or more kinds thereof are used in combination, asymmetrical dithienyl sulfide disulfonium salts can be produced.

A commercially available sulfoxide may be used as it is, or an appropriately produced sulfoxide may be used. There is no particular limitation on a method for producing the sulfoxide. When the sulfoxide is bis(4-methylphenyl) sulfoxide in which both $R^{5a}$ and $R^{6a}$ in the formula (A2) are 4-methylphenyl groups, the sulfoxide can be produced by a known method such as a method of reacting toluene with thionyl chloride in the presence of trifluoromethanesulfonic acid (Synlett., 1999, 1397). When sulfoxide is 4-methylphenyl-(2,4-dimethylphenyl)sulfoxide in which $R^{5a}$ in the formula (A2) is a 4-methylphenyl group and $R^{6a}$ is a 2,4-dimethylphenyl group, the sulfoxide can be produced by a known method such as a method of reacting m-xylene with p-toluenesulfinyl chloride in the presence of aluminum chloride (J. Org. Chem., 1974, 39, 1203).

The 2,2'-dithienyl sulfide can be produced by a known method. Specifically, it can be produced, for example, by reacting 2-bromothiophene with 2-thiophenethiol in the presence of a copper oxide (I) catalyst (J. Org. Chem., 1996, 61, 7608). It is also possible to produce by a method of reacting 2-iodothiophene as an iodinated aromatic compound with 2-thiophenethiol as an aromatic thiol in the method of reacting an iodinated aromatic compound with an aromatic thiol in the presence of copper (I) iodide and a neocuproin catalyst known as a usual method of producing an aromatic sulfide compound (Org. Lett., 2002, 4, 2803).

The amount of sulfoxide used is not particularly limited and is preferably from 1.5 to 4 mol, more preferably from 1.6 to 3.5 mol, and particularly preferably from 1.8 to 3 mol, based on 1 mol of 2,2'-dithienyl sulfide in view of an improvement in yield and economical efficiency.

Examples of the condensing agent include, but are not particularly limited to, acetic anhydride, trifluoroacetic anhydride, concentrated sulfuric acid, diphosphorus pentaoxide, and polyphosphoric acid. Of these condensing agents, acetic anhydride, concentrated sulfuric acid and diphosphorus pentaoxide are preferably used. These condensing agents may be used alone, or two or more kinds thereof may be used in combination.

The amount of the condensing agent used is not particularly limited and is preferably from 1 to 40 mol, and more preferably from 1 to 30 mol, based on 1 mol of 2,2'-dithienyl sulfide. When the amount of the condensing agent is less than 1 mol, the yield may decrease. In contrast, when the amount of the condensing agent is more than 40 mol, it is not economical because the effect corresponding to the amount of use is not exerted.

Examples of the strong acid include, but are not particularly limited to, methanesulfonic acid, ethanesulfonic acid, and trifluoromethanesulfonic acid. Of these strong acids, methanesulfonic acid is preferably used. These strong acids may be used alone, or two or more kinds thereof may be used in combination.

The amount of the strong acid used is not particularly limited and is preferably from 1 to 50 mol, and more preferably from 2 to 30 mol, based on 1 mol of 2,2'-dithienyl sulfide. When the amount of the strong acid is less than 1 mol, the yield may decrease. In contrast, when the amount of the strong acid is more than 50 mol, it is not economical because the effect corresponding to the amount of use is not exerted and volume efficiency deteriorates.

In the reaction of condensing sulfoxide with 2,2'-dithienyl sulfide in the presence of a condensing agent and a strong acid, a reaction solvent is not necessarily required. For the purpose of improving stirring efficiency, a solvent such as sulfolane, dichloromethane or chloroform may be used as the reaction solvent. The amount of the reaction solvent used is preferably from 30 to 3,000 parts by weight, and more preferably from 50 to 2,000 parts by weight, based on 100 parts by weight of 2,2'-dithienyl sulfide.

There is no particular limitation on the operation in the condensation reaction. For example, there is exemplified a method of adding dropwise a predetermined amount of the strong acid while mixing and stirring a predetermined amount of the sulfoxide, 2,2'-dithienyl sulfide, a condensing agent and, if necessary, the reaction solvent.

The reaction temperature is preferably from −20 to 100° C., and more preferably from −10 to 80° C. When the reaction temperature is lower than −20° C., the reaction may require a long time because the reaction rate decreases. In contrast, when the reaction temperature is higher than 100° C., the side reaction is likely to arise and thus the yield and purity may decrease. The reaction time varies depending on the reaction temperature and is usually from 0.5 to 48 hours, and preferably from 1 to 24 hours.

The dithienyl sulfide disulfonium salt represented by the formula (A1) can be produced by condensing sulfoxide with 2,2'-dithienyl sulfide, and reacting the condensation reaction product with an alkali metal salt of the inorganic acid or an alkali metal salt of the organic acid.

Specific examples of the alkali metal salt of the inorganic acid include sodium hexafluoroantimonate, potassium hexafluoroantimonate, sodium hexafluoroarsenate, potassium hexafluoroarsenate, sodium hexafluorophosphate, potassium hexafluorophosphate, sodium pentafluorohydroxoantimonate, potassium pentafluorohydroxoantimonate, sodium tetrafluoroborate, potassium tetrafluoroborate, lithium tetrakis(pentafluorophenyl)borate, sodium tetrakis(pentafluorophenyl)borate, potassium tetrakis(pentafluorophenyl)borate, lithium tetrakis(trifluoromethylphenyl)borate, sodium tetrakis(trifluoromethylphenyl)borate, potassium tetrakis(trifluoromethylphenyl)borate, lithium trifluoro(pentafluorophenyl)borate, sodium trifluoro(pentafluorophenyl)borate, potassium trifluoro(pentafluorophenyl)borate, lithium tetrakis(difluorophenyl)borate, sodium tetrakis(difluorophenyl)borate, potassium tetrakis(difluorophenyl)borate, lithium difluorobis(pentafluorophenyl)borate, sodium difluorobis(pentafluorophenyl)borate, and potassium difluorobis(pentafluorophenyl)borate.

Specific examples of the alkali metal salt of the organic acid include sodium methanesulfonate, potassium methanesulfonate, sodium ethanesulfonate, potassium ethanesulfonate, sodium propanesulfonate, potassium propanesulfonate, sodium butanesulfonate, potassium butanesulfonate, sodium octanesulfonate, potassium octanesulfonate, sodium trifluoromethanesulfonate, potassium trifluoromethanesulfonate, sodium perfluorobutanesulfonate, potassium perfluorobutanesulfonate, sodium benzenesulfonate, potassium benzenesulfonate, sodium benzene-1,3-disulfonate, potassium benzene-1,3-disulfonate, sodium p-toluenesulfonate, potassium p-toluenesulfonate, sodium anthraquinone-1-sulfonate, potassium anthraquinone-1-sulfonate, sodium anthraquinone-2-sulfonate, potassium anthraquinone-2-sulfonate, sodium anthraquinone-1,5-disulfonate, potassium anthraquinone-1,5-disulfonate, sodium methane carboxylate, potassium methane carboxylate, sodium ethane carboxylate, potassium ethane carboxylate, sodium propane carboxylate, potassium propane carboxylate, sodium butane carboxylate, potassium butane carboxylate, sodium octane carboxylate, potassium octane carboxylate, sodium trifluoromethane carboxylate, potassium trifluoromethane carboxylate, sodium benzene carboxylate, potassium benzene carboxylate, sodium p-toluene carboxylate, potassium p-toluene carboxylate, lithium bis(trifluoromethanesulfonyl)imide, and lithium tris(trifluoromethanesulfonyl)methide.

Of these alkali metal salts, sodium hexafluorophosphate, potassium hexafluorophosphate, lithium tetrakis(pentafluorophenyl)borate, sodium tetrakis(pentafluorophenyl)borate, potassium tetrakis(pentafluorophenyl)borate, sodium trifluoromethanesulfonate, potassium trifluoromethanesulfonate, sodium perfluorobutanesulfonate, and potassium perfluorobutanesulfonate are preferred in view of acid strength and safety of an acid generated by using the resultant dithienyl sulfide disulfonium salt as a photoacid generator.

The amount of the alkali metal salt used is not particularly limited and is preferably from 1.5 to 4 mol, and more preferably from 1.6 to 3 mol, based on 1 mol of 2,2'-dithienyl sulfide. When the amount of the alkali metal salt is less than 1.5 mol, the yield may decrease. In contrast, when the amount of the alkali metal salt is more than 4 mol, it is not economical because the effect corresponding to the amount of use is not exerted. Both the alkali metal salt of the inorganic and the alkali metal salt of the organic acid can be used as an aqueous solution. The concentration in the case of using as the aqueous solution is preferably from 1 to 80% by weight, and more preferably from 3 to 50% by weight.

There is no particular limitation on the operation in the reaction of the condensation reaction product with the alkali metal salt. Examples of the method used in the operation in the reaction include a method of adding a predetermined amount of the alkali metal salt to the reaction solution after the condensation reaction, a method of adding the reaction solution after the condensation reaction to a predetermined amount of the alkali metal salt, a method of adding the reaction solution after the condensation reaction to a predetermined amount of water to form an aqueous solution of the condensation reaction product and adding an alkali metal salt, and a method of adding the reaction solution after the condensation reaction to a predetermined amount of water to form an aqueous solution of the condensation reaction product and adding the aqueous solution to an alkali metal salt. In the case of these operations, an organic solvent such as monochlorobenzene, ethyl acetate or dichloromethane may exist.

The reaction temperature is preferably from −10 to 100° C., and more preferably from 0 to 80° C. When the reaction temperature is lower than −10° C., the reaction may require a long time because the reaction rate decreases. In contrast, when the reaction temperature is higher than 100° C., the side reaction is likely to arise and thus the yield and purity may decrease.

The dithienyl sulfide disulfonium salt thus obtained can be isolated by a method of filtering a solid precipitated after the completion of the reaction, or a method of extracting with an organic solvent such as monochlorobenzene, ethyl acetate or dichloromethane and distilling off the organic solvent. The dithienyl sulfide disulfonium salt can be optionally purified by a conventional method such as recrystallization from a solvent such as monochlorobenzene, toluene, ethyl acetate, acetone, methanol, ethanol, isopropanol, n-heptane, or water, an activated carbon treatment, or column purification.

The dithienyl sulfide sulfonium salt according to the second aspect of the present invention is a compound represented by the following formula (B1).

[Chemical Formula 7]

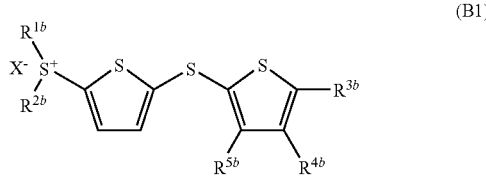

(B1)

In the formula (B1), $R^{1b}$ and $R^{2b}$ each independently represents an optionally substituted monocyclic carbon ring group, an optionally substituted condensed polycyclic carbon ring group or an optionally substituted monocyclic heterocyclic group, $R^{ab}$ to $R^{5b}$ each independently represents a hydrogen atom, an alkyl group having 1 to 10 carbon atoms, an alkoxy group having 1 to 4 carbon atoms, an acyl group or a hydroxyl group, and $X^-$ represents an inorganic acid ion or an organic acid ion Examples of the optionally substituted monocyclic phenyl group and a phenyl group having a substituent.

Examples of the optionally substituted condensed polycyclic carbon ring group include a naphthyl group and a naphthyl group having a substituent.

Examples of the optionally substituted monocyclic heterocyclic group include a thienyl group and a thienyl group having a substituent.

Examples of the substituent include a hydroxyl group, an acetoxy group, a phenyl group, an alkyl group having 1 to 10 carbon atoms, an alkoxy group having 1 to 4 carbon atoms, an alkylthio group having 1 to 4 carbon atoms, and a halogen atom.

Examples of the alkyl group having 1 to 10 carbon atoms include a methyl group, an ethyl group, a propyl group, a butyl group, a pentyl group, a hexyl group, an octyl group, and a decyl group.

Examples of the alkoxy group having 1 to 4 carbon atoms include a methoxy group, an ethoxy group, a propoxy group, a butoxy group, and a methoxyethoxy group.

Examples of the alkylthio group having 1 to 4 carbon atoms include a methylthio group, an ethylthio group, a propylthio group, and a butylthio group.

Examples of the halogen atom include a fluorine atom, a chlorine atom, a bromine atom, and an iodine atom.

As the group represented by $R^{1b}$ and $R^{2b}$ in the formula (B1), an optionally substituted monocyclic carbon ring group is preferably used, and a phenyl group and a phenyl group having a substituent are more preferably used. As the substituent in the phenyl group having a substituent, a methyl group, an ethyl group, an n-propyl group, an isopropyl group, an n-butyl group, a tert-butyl group, a methoxy group, an ethoxy group, an n-propoxy group, an isopropoxy group, an n-butoxy group, an isobutoxy group, a sec-butoxy group, a tert-butoxy group, a methylthio group and a fluorine atom are preferably used, and a methyl group, an ethyl group, an n-propyl group, a isopropyl group, an n-butyl group, a methoxy group, an ethoxy group, an n-propoxy group, an isopropoxy group and an n-butoxy group are more preferably used.

The optionally substituted monocyclic carbon ring group, the optionally substituted condensed polycyclic carbon ring group and the optionally substituted monocyclic heterocyclic group may have one substituent or may have a plurality of substituents. In the case of having a plurality of substituents, the substituent may be the same or different.

Examples of the alkyl group having 1 to 10 carbon atoms represented by $R^{3b}$ to $R^{5b}$ in the formula (B1) include a methyl group, an ethyl group, a propyl group, a butyl group, a pentyl group, a hexyl group, an octyl group, and a decyl group.

Examples of the alkoxy group having 1 to 4 carbon atoms represented by $R^{3b}$ to $R^{5b}$ include a methoxy group, an ethoxy group, a propoxy group, and a butoxy group.

Examples of the acyl group represented by $R^{3b}$ to $R^{5b}$ include an acetyl group, a formyl group, and a benzoyl group.

As the group represented by $R^{3b}$ to $R^{5b}$ in the formula (B1), a hydrogen atom, a methyl group, an ethyl group, an n-propyl group, an n-butyl group, a methoxy group, an ethoxy group, an n-propoxy group, an n-butoxy group and an acetyl group are preferably used.

Examples of the inorganic acid ion represented by $X^-$ in the formula (B1) include, but are not particularly limited to, a hexafluoroantimonic acid ion, a hexafluoroarsenic acid ion, a hexafluorophosphoric acid ion, a pentafluorohydroxoantimonic acid ion, a tetrafluoroboric acid ion, a tetrakis(pentafluorophenyl)boric acid ion, a tetrakis(trifluoromethylphenyl)boric acid ion, a trifluoro(pentafluorophenyl)boric acid ion, a tetrakis(difluorophenyl)boric acid ion, and a difluorobis(pentafluorophenyl)boric acid ion.

Examples of the organic acid ion represented by $X^-$ in the formula (B1) include, but are not particularly limited to, a methanesulfonic acid ion, an ethanesulfonic acid ion, a propanesulfonic acid ion, a butanesulfonic acid ion, an octanesulfonic acid ion, a trifluoromethanesulfonic acid ion, a perfluorobutanesulfonic acid ion, a perfluorohexanesulfonic acid ion, a benzenesulfonic acid ion, a benzene-1,3-disulfonic acid ion, a p-toluenesulfonic acid ion, an anthraquinone-1-sulfonic acid ion, an anthraquinone-2-sulfonic acid ion, an anthraquinone-1,5-disulfonic acid ion, a methanecarboxylic acid ion, an ethanecarboxylic acid ion, a propanecarboxylic acid ion, a butanecarboxylic acid ion, an octanecarboxylic acid ion, a trifluoromethanecarboxylic acid ion, a benzenecarboxylic acid ion, a p-toluenecarboxylic acid ion, a bis(trifluoromethanesulfonyl)imide ion, and a tris(trifluoromethanesulfonyl)methide ion.

Of these acid ions, a hexafluorophosphoric acid ion, a tetrakis(pentafluorophenyl)boric acid ion, a trifluoromethanesulfonic acid ion and a perfluorobutanesulfonic acid ion are preferably used in view of acid strength and safety of an acid generated when the dithienyl sulfide sulfonium salt is used as the photoacid generator.

Specific examples of the dithienyl sulfide sulfonium salt according to the second aspect of the present invention include diphenyl[5-(thiophen-2-ylthio)-thiophen-2-yl]sulfonium perfluorobutanesulfonate, diphenyl[5-(thiophen-2-ylthio)-thiophen-2-yl]sulfonium trifluoromethanesulfonate, diphenyl[5-(thiophen-2-ylthio)-thiophen-2-yl]sulfonium hexafluorophosphate, diphenyl[5-(thiophen-2-ylthio)-thiophen-2-yl]sulfonium tetrakis(pentafluorophenyl)borate, bis(4-methylphenyl)[5-(thiophen-2-ylthio)-thiophen-2-yl]sulfonium perfluorobutanesulfonate, bis(4-methylphenyl)[5-(thiophen-2-ylthio)-thiophen-2-yl]sulfonium trifluoromethanesulfonate, bis(4-methylphenyl)[5-(thiophen-2-ylthio)-thiophen-2-yl]sulfonium hexafluorophosphate, bis(4-methylphenyl)[5-(thiophen-2-ylthio)-thiophen-2-yl]sulfonium tetrakis(pentafluorophenyl)borate, bis(4-methoxyphenyl)[5-(thiophen-2-ylthio)-thiophen-2-yl]sulfonium perfluorobutanesulfonate, bis(4-methoxyphenyl)[5-(thiophen-2-ylthio)-thiophen-2-yl]sulfonium trifluoromethanesulfonate, bis(4-methoxyphenyl)[5-(thiophen-2-ylthio)-thiophen-2-yl]sulfonium hexafluorophosphate, bis(4-methoxyphenyl)[5-(thiophen-2-ylthio)-thiophen-2-yl]sulfonium tetrakis(pentafluorophenyl)borate, bis(4-isopropoxyphenyl)[5-(thiophen-2-ylthio)-thiophen-2-yl]sulfonium perfluorobutanesulfonate, bis(4-isopropoxyphenyl)[5-(thiophen-2-ylthio)-thiophen-2-yl]sulfonium trifluoromethanesulfonate, bis(4-isopropoxyphenyl)[5-(thiophen-2-ylthio)-thiophen-2-yl]sulfonium hexafluorophosphate, bis(4-isopropoxyphenyl)[5-(thiophen-2-ylthio)-thiophen-2-yl]sulfonium tetrakis(pentafluorophenyl)borate, bis(4-n-butoxyphenyl)[5-(thiophen-2-ylthio)-thiophen-2-yl]sulfonium perfluorobutanesulfonate, bis(4-n-butoxyphenyl)[5-(thiophen-2-ylthio)-thiophen-2-yl]sulfonium trifluoromethanesulfonate, bis(4-n-butoxyphenyl)[5-(thiophen-2-ylthio)-thiophen-2-yl]sulfonium hexafluorophosphate, bis(4-n-butoxyphenyl)[5-(thiophen-2-ylthio)-thiophen-2-yl]sulfonium tetrakis(pentafluorophenyl)borate, [5-(5-methyl-thiophen-2-ylthio)-thiophen-2-yl]diphenylsulfonium perfluorobutanesulfonate, [5-(5-methyl-thiophen-2-ylthio)-thiophen-2-yl]diphenylsulfonium trifluoromethanesulfonate, [5-(5-methyl-thiophen-2-ylthio)-thiophen-2-yl]diphenylsulfonium hexafluorophosphate, [5-(5-methyl-thiophen-2-ylthio)-thiophen-2-yl]diphenylsulfonium tetrakis(pentafluorophenyl)borate, bis(4-methylphenyl)[5-(5-methyl-thiophen-2-ylthio)-thiophen-2-yl]sulfonium perfluorobutanesulfonate, bis(4-methylphenyl)[5-(5-methyl-thiophen-2-ylthio)-thiophen-2-yl]sulfonium trifluoromethanesulfonate, bis(4-methylphenyl)[5-(5-methyl-thiophen-2-ylthio)-thiophen-2-yl]sulfonium hexafluorophosphate, bis(4-methylphenyl)[5-(5-methyl-thiophen-2-ylthio)-thiophen-2-yl]sulfonium tetrakis(pentafluorophenyl)borate, bis(4-methoxyphenyl)[5-(5-methyl-thiophen-2-ylthio)-thiophen-2-yl]sulfonium perfluorobutanesulfonate, bis(4-methoxyphenyl)[5-(5-methyl-thiophen-2-ylthio)-thiophen-2-yl]sulfonium trifluoromethanesulfonate, bis(4-methoxyphenyl)[5-(5-methyl-thiophen-2-ylthio)-thiophen-2-yl]sulfonium hexafluorophosphate, bis(4-methoxyphenyl)[5-(5-methyl-thiophen-2-ylthio)-thiophen-2-yl]sulfonium tetrakis(pentafluorophenyl)borate, [5-(5-methoxy-thiophen-2-ylthio)-thiophen-2-yl]diphenylsulfonium perfluorobutanesulfonate, [5-(5-methoxy-thiophen-2-ylthio)-thiophen-2-yl]diphenylsulfonium trifluoromethanesulfonate, [5-(5-methoxy-thiophen-2-ylthio)-thiophen-2-yl]diphenylsulfonium hexafluorophosphate, [5-(5-methoxy-thiophen-2-ylthio)-thiophen-2-yl]diphenylsulfonium tetrakis(pentafluorophenyl)borate, [5-(5-methoxy-thiophen-2-ylthio)-thiophen-2-yl]bis(4-methylphenyl)sulfonium perfluorobutanesulfonate, [5-(5-methoxy-thiophen-2-ylthio)-thiophen-2-yl]bis(4-methylphenyl)sulfonium trifluoromethanesulfonate, [5-(5-methoxy-thiophen-2-ylthio)-thiophen-2-yl]bis(4-methylphenyl)sulfonium hexafluorophosphate, [5-(5-methoxy-thiophen-2-ylthio)-thiophen-2-yl]bis(4-methylphenyl)sulfonium tetrakis(pentafluorophenyl)borate, bis(4-methoxyphenyl)-[5-(5-methoxy-thiophen-2-ylthio)-thiophen-2-yl]sulfonium perfluorobutanesulfonate, bis(4-methoxyphenyl)-[5-(5-methoxy-thiophen-2-ylthio)-thiophen-2-yl]sulfonium trifluoromethanesulfonate, bis(4-methoxyphenyl)-[5-(5-methoxy-thiophen-2-ylthio)-thiophen-2-yl]sulfonium hexafluorophosphate, bis(4-methoxyphenyl)-[5-(5-methoxy-thiophen-2-ylthio)-thiophen-2-yl]sulfonium tetrakis(pentafluorophenyl)borate, [5-(5-acetyl-thiophen-2-ylthio)-thiophen-2-yl]diphenylsulfonium perfluorobutanesulfonate, [5-(5-acetyl-thiophen-2-ylthio)-thiophen-2-yl]diphenylsulfonium trifluoromethanesulfonate, [5-(5-acetyl-thiophen-2-ylthio)-thiophen-2-yl]diphenylsulfonium hexafluorophosphate, [5-(5-acetyl-thiophen-2-ylthio)-thiophen-2-yl]diphenylsulfonium tetrakis(pentafluorophenyl)borate, [5-(5-acetyl-thiophen-2-ylthio)-thiophen-2-yl]bis(4-methylphenyl)sulfonium perfluorobutanesulfonate, [5-(5-acetyl-thiophen-2-ylthio)-thiophen-2-yl]bis(4-methylphenyl)sulfonium trifluoromethanesulfonate, [5-(5-acetyl-thiophen-2-ylthio)-thiophen-2-yl]bis(4-methylphenyl)sulfonium hexafluorophosphate, [5-(5-acetyl-thiophen-2-ylthio)-thiophen-2-yl]bis(4-methylphenyl)sulfonium tetrakis(pentafluorophenyl)borate, [5-(5-acetyl-thiophen-2-ylthio)-thiophen-2-yl]bis(4-methoxyphenyl)sulfonium perfluorobutanesulfonate, [5-(5-acetyl-thiophen-2-ylthio)-thiophen-2-yl]bis(4-methoxyphenyl)sulfonium trifluoromethanesulfonate, [5-(5-acetyl-thiophen-2-ylthio)-thiophen-2-yl]bis(4-methoxyphenyl)sulfonium hexafluorophosphate, and [5-(5-acetyl-thiophen-2-ylthio)-thiophen-2-yl]bis(4-methoxyphenyl)sulfonium tetrakis(pentafluorophenyl)borate.

The dithienyl sulfide sulfonium salt represented by the formula (B1) can be produced, for example, by a method of condensing sulfoxide represented by the following formula (B2):

[Chemical Formula 8]

(B2)

wherein $R^{1b}$ and $R^{2b}$ each represents the same groups as those for $R^{1b}$ and $R^{2b}$ in the formula (B1), with a dithienyl sulfide compound represented by the following formula (B3):

[Chemical Formula 9]

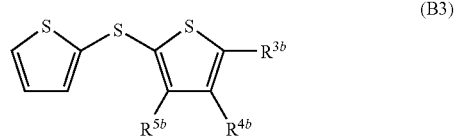

(B3)

wherein $R^{3b}$ to $R^{5b}$ each represents the same group as that for $R^{3b}$ to $R^{5b}$ in the formula (B1), in the presence of a condensing agent and a strong acid, and reacting the condensation reaction product with an alkali metal salt of an inorganic acid corresponding to the inorganic acid ion, or an alkali metal salt of an organic acid corresponding to the organic acid ion.

Specific examples of the sulfoxide represented by the formula (B2) include diphenyl sulfoxide, bis(4-methylphenyl) sulfoxide, bis(4-ethylphenyl)sulfoxide, bis(4-n-propylphenyl)sulfoxide, bis(4-isopropylphenyl) sulfoxide, bis(4-n-butylphenyl)sulfoxide, bis(4-tert-butylphenyl)sulfoxide, bis(4-phenylphenyl)sulfoxide, bis(4-methoxyphenyl)sulfoxide, bis(4-ethoxyphenyl) sulfoxide, bis(4-n-propoxyphenyl)sulfoxide, bis(4-isopropoxyphenyl)sulfoxide, bis(4-n-butoxyphenyl) sulfoxide, bis(4-isobutoxyphenyl)sulfoxide, bis(4- sec-butoxyphenyl)sulfoxide, bis(4-tert-butoxyphenyl) sulfoxide, bis(4-methylthiophenyl)sulfoxide, bis(4-ethylthiophenyl) sulfoxide, bis(4-n-propylthiophenyl) sulfoxide, bis(4-isopropylthiophenyl)sulfoxide, bis(4-n-butylthiophenyl) sulfoxide, bis(4-tert-butylthiophenyl) sulfoxide, bis(4-hydroxyphenyl)sulfoxide, bis(4-acetoxyphenyl)sulfoxide, bis(4-fluorophenyl)sulfoxide, bis (4-chlorophenyl)sulfoxide, bis(4-bromophenyl)sulfoxide, bis(4-iodophenyl)sulfoxide, bis(2,4-dimethylphenyl)sulfoxide, bis(3,4-dimethylphenyl)sulfoxide, bis(2,4,6-trimethylphenyl)sulfoxide, di-(2-thienyl)sulfoxide, and di-(2-naphthyl)sulfoxide.

Of these sulfoxides, diphenyl sulfoxide, bis(4-methylphenyl)sulfoxide, bis(4-ethylphenyl)sulfoxide, bis(4-n-propylphenyl)sulfoxide, bis(4-isopropylphenyl)sulfoxide, bis(4-n-butylphenyl)sulfoxide, bis(4-methoxyphenyl)sulfoxide, bis (4-ethoxyphenyl)sulfoxide, bis(4-n-propoxyphenyl) sulfoxide, bis(4-isopropoxyphenyl)sulfoxide, bis(4-n-butoxyphenyl)sulfoxide, bis(4-methylthiophenyl)sulfoxide, bis(4-fluorophenyl)sulfoxide and bis(2,4-dimethylphenyl) sulfoxide are preferably used.

A commercially available sulfoxide may be used as it is, or an appropriately produced sulfoxide may be used. There is no particular limitation on a method for producing the sulfoxide. When the sulfoxide is bis(4-methylphenyl)sulfoxide in which both $R^{1b}$ and $R^{2b}$ in the formula (B2) are 4-methylphenyl groups, the sulfoxide can be produced by a known method such as a method of reacting toluene with thionyl chloride in the presence of trifluoromethanesulfonic acid (Synlett., 1999, 1397). When sulfoxide is 4-methylphenyl-(2,4-dimethylphenyl)sulfoxide in which $R^{1b}$ in the formula (B2) is a 4-methylphenyl group and $R^{2b}$ is a 2,4-dimethylphenyl group, the sulfoxide can be produced by a known method such as a method of reacting m-xylene with p-toluenesulfinyl chloride in the presence of aluminum chloride (J. Org. Chem., 1974, 39, 1203).

Specific examples of the dithienyl sulfide compound represented by the formula (B3) include 2,2'-dithienyl sulfide, 2-methyl-5-(thiophen-2-ylthio)-thiophene, 2-ethyl-5-(thiophen-2-ylthio)-thiophene, 2-n-propyl-5-(thiophen-2-ylthio)-thiophene, 2-isopropyl-5-(thiophen-2-ylthio)-thiophene, 2-n-butyl-5-(thiophen-2-ylthio)-thiophene, 2-isobutyl-5-(thiophen-2-ylthio)-thiophene, 2-methoxy-5-(thiophen-2-ylthio)-thiophene, 2-ethoxy-5-(thiophen-2-ylthio)-thiophene, 2-n-propoxy-5-(thiophen-2-ylthio)-thiophene, 2-isopropoxy-5-(thiophen-2-ylthio)-thiophene, 2-n-butoxy-5-(thiophen-2-ylthio)-thiophene, 2-isobutoxy-5-(thiophen-2-ylthio)-thiophene, 2-acetyl-5-(thiophen-2-ylthio)-thiophene, 2-benzoyl-5-(thiophen-2-ylthio)-thiophene, and 2-hydroxy-5-(thiophen-2-ylthio)-thiophene.

Of these dithienyl sulfide compounds, 2,2'-dithienyl sulfide, 2-methyl-5-(thiophen-2-ylthio)-thiophene, 2-ethyl-5-(thiophen-2-ylthio)-thiophene, 2-n-propyl-5-(thiophen-2-ylthio)-thiophene, 2-n-butyl-5-(thiophen-2-ylthio)-thiophene, 2-methoxy-5-(thiophen-2-ylthio)-thiophene, 2-ethoxy-5-(thiophen-2-ylthio)-thiophene, 2-n-propoxy-5-(thiophen-2-ylthio)-thiophene, 2-n-butoxy-5-(thiophen-2-ylthio)-thiophene, and 2-acetyl-5-(thiophen-2-ylthio)-thiophene are preferably used.

The dithienyl sulfide compound can be produced by a known method. Specifically, the dithienyl sulfide compound can be produced, for example, by reacting 2-bromothiophene with 2-thiophenethiol in the presence of a copper oxide(I) catalyst (J. Org. Chem., 1996, 61, 7608) when the dithienyl sulfide compound is 2,2'-dithienyl sulfide in which all of $R^{3b}$ to $R^{5b}$ in the formula (B3) are hydrogen atoms. It is also possible to produce by a method of reacting 2-iodothiophene as an iodinated aromatic compound with 2-thiophenethiol as an aromatic thiol in the method of reacting an iodinated aromatic compound with an aromatic thiol in the presence of copper (I) iodide and a neocuproin catalyst (Org. Lett., 2002, 4, 2803) known as a usual method of producing an aromatic sulfide compound.

Similarly, when dithienyl sulfide compound is 2-methyl-5-(thiophen-2-ylthio)-thiophene in which $R^{3b}$ in the formula (B3) is a methyl group, and both $R^{4b}$ and $R^{5b}$ are hydrogen atoms, it can be produced by a method of reacting 2-bromo-5-methylthiophene with 2-thiophenethiol in the presence of a copper oxide (I) catalyst.

There is no particular limitation on the amount of the sulfoxide. In view of an improvement in yield and economical efficiency, the amount of the sulfoxide is preferably 0.6 mol or more and less than 1.5 mol, more preferably 0.8 mol or more and less than 1.5 mol, and still more preferably 0.9 mol or more and less than 1.5 mol, based on 1 mol of the dithienyl sulfide compound represented by the formula (B3).

Examples of the condensing agent include, but are not particularly limited to, acetic anhydride, trifluoroacetic anhydride, concentrated sulfuric acid, diphosphorus pentaoxide, and polyphosphoric acid. Of these condensing agents, acetic anhydride, concentrated sulfuric acid and diphosphorus pentaoxide are preferably used. These condensing agents may be used alone, or two or more kinds thereof may be used in combination.

The amount of the condensing agent used is not particularly limited and is preferably from 1 to 40 mol, and more preferably from 1 to 30 mol, based on 1 mol of the dithienyl sulfide compound. When the amount of the condensing agent is less than 1 mol, the yield may decrease. In contrast, when the amount of the condensing agent is more than 40 mol, it is not economical because the effect corresponding to the amount of use is not exerted.

Examples of the strong acid include, but are not particularly limited to, methanesulfonic acid, ethanesulfonic acid and trifluoromethanesulfonic acid. Of these strong acids, methanesulfonic acid is preferably used. These strong acids may be used alone, or two or more kinds thereof may be used in combination.

The amount of the strong acid used is not particularly limited and is preferably from 1 to 50 mol, and more preferably from 2 to 30 mol, based on 1 mol of the dithienyl sulfide compound. When the amount of the strong acid is less than 1 mol, the yield may decrease. In contrast, when the amount of the strong acid is more than 50 mol, it is not economical because the effect corresponding to the amount of use is not exerted and volume efficiency deteriorates.

In the reaction of condensing sulfoxide with the dithienyl sulfide compound in the presence of a condensing agent and a strong acid, a reaction solvent is not necessarily required. For the purpose of improving stirring efficiency, a solvent such as sulfolane, dichloromethane or chloroform may be used as the reaction solvent. The amount of the reaction solvent is preferably from 30 to 3,000 parts by weight, and more preferably from 50 to 2,000 parts by weight, based on 100 parts by weight of the dithienyl sulfide compound.

There is no particular limitation on the operation in the condensation reaction. For example, there is exemplified a method of adding dropwise a predetermined amount of the strong acid while mixing and stirring a predetermined amount of the sulfoxide, the dithienyl sulfide compound, the condensing agent and, if necessary, the reaction solvent.

The reaction temperature is preferably from −20 to 100° C., and more preferably from −10 to 80° C. When the reaction temperature is lower than −20° C., the reaction may require a long time because the reaction rate decreases. In contrast, when the reaction temperature is higher than 100° C., the side reaction is likely to arise and thus the yield and purity may decrease. The reaction time varies depending on the reaction temperature and is usually from 0.5 to 48 hours, and preferably from 1 to 24 hours.

The dithienyl sulfide sulfonium salt represented by the formula (B1) can be produced by condensing sulfoxide with a dithienyl sulfide compound, and reacting the condensation reaction product with an alkali metal salt of the inorganic acid or an alkali metal salt of the organic acid.

Specific examples of the alkali metal salt of the inorganic acid include sodium hexafluoroantimonate, potassium hexafluoroantimonate, sodium hexafluoroarsenate, potassium hexafluoroarsenate, sodium hexafluorophosphate, potassium hexafluorophosphate, sodium pentafluorohydroxoantimonate, potassium pentafluorohydroxoantimonate, sodium tetrafluoroborate, potassium tetrafluoroborate, lithium tetrakis(pentafluorophenyl)borate, sodium tetrakis(pentafluorophenyl)borate, potassium tetrakis(pentafluorophenyl)borate, lithium tetrakis(trifluoromethylphenyl)borate, sodium tetrakis(trifluoromethylphenyl)borate, potassium tetrakis(trifluoromethylphenyl)borate, lithium trifluoro(pentafluorophenyl)borate, sodium trifluoro(pentafluorophenyl)borate, potassium trifluoro(pentafluorophenyl)borate, lithium tetrakis(difluorophenyl)borate, sodium tetrakis(difluorophenyl)borate, potassium tetrakis(difluorophenyl)borate, lithium difluorobis(pentafluorophenyl)borate, sodium difluorobis(pentafluorophenyl)borate, and potassium difluorobis(pentafluorophenyl)borate.

Specific examples of the alkali metal salt of the organic acid include sodium methanesulfonate, potassium methanesulfonate, sodium ethanesulfonate, potassium ethanesulfonate, sodium propanesulfonate, potassium propanesulfonate, sodium butanesulfonate, potassium butanesulfonate, sodium octanesulfonate, potassium octanesulfonate, sodium trifluoromethanesulfonate, potassium trifluoromethanesulfonate, sodium perfluorobutanesulfonate, potassium perfluorobutanesulfonate, sodium benzenesulfonate, potassium benzenesulfonate, sodium benzene-1,3-disulfonate, potassium benzene-1,3-disulfonate, sodium p-toluenesulfonate, potassium p-toluenesulfonate, sodium anthraquinone-1-sulfonate, potassium anthraquinone-1-sulfonate, sodium anthraquinone-2-sulfonate, potassium anthraquinone-2-sulfonate, sodium anthraquinone-1,5-disulfonate, potassium anthraquinone-1,5-disulfonate, sodium methane carboxylate, potassium methane carboxylate, sodium ethane carboxylate, potassium ethane carboxylate, sodium propane carboxylate, potassium propane carboxylate, sodium butane carboxylate, potassium butane carboxylate, sodium octane carboxylate, potassium octane carboxylate, sodium trifluoromethane carboxylate, potassium trifluoromethane carboxylate, sodium benzene carboxylate, potassium benzene carboxylate, sodium p-toluene carboxylate, potassium p-toluene carboxylate, lithium bis(trifluoromethanesulfonyl)imide, and lithium tris(trifluoromethanesulfonyl)methide.

Of these alkali metal salts, sodium hexafluorophosphate, potassium hexafluorophosphate, lithium tetrakis(pentafluorophenyl)borate, sodium tetrakis(pentafluorophenyl)borate, potassium tetrakis(pentafluorophenyl)borate, sodium trifluoromethanesulfonate, potassium trifluoromethanesulfonate, sodium perfluorobutanesulfonate and potassium perfluorobutanesulfonate are preferable in view of acid strength and safety of an acid generated when the dithienyl sulfide sulfonium salt is used as the photoacid generator.

The amount of the alkali metal salt used is not particularly limited and is preferably from 0.6 to 1.8 mol, and more preferably from 0.8 to 1.6 mol, based on 1 mol of the dithienyl sulfide compound. When the amount of the alkali metal salt is less than 0.6 mol, the yield may decrease. In contrast, when the amount of the alkali metal salt is more than 1.8 mol, it is not economical because the effect corresponding to the amount of use is not exerted. Both the alkali metal salt of the inorganic and the alkali metal salt of the organic acid can be used as an aqueous solution. The concentration in the case of using as the aqueous solution is preferably from 1 to 80% by weight, and more preferably from 3 to 50% by weight.

There is no particular limitation on the operation in the reaction of the condensation reaction product with the alkali metal salt. Examples of the method used in the operation in the reaction include a method of adding a predetermined amount of the alkali metal salt to the reaction solution after the condensation reaction, a method of adding the reaction solution after the condensation reaction to a predetermined amount of the alkali metal salt, a method of adding the reaction solution after the condensation reaction to a predetermined amount of water to form an aqueous solution of the condensation reaction product and adding an alkali metal salt, and a method of adding the reaction solution after the condensation reaction to a predetermined amount of water to form an aqueous solution of the condensation reaction product and adding the aqueous solution to an alkali metal salt. In the case of these operations, an organic solvent such as monochlorobenzene, ethyl acetate or dichloromethane may exist.

The reaction temperature is preferably from −10 to 100° C., and more preferably from 0 to 80° C. When the reaction temperature is lower than −10° C., the reaction may require a long time because the reaction rate decreases. In contrast, when the reaction temperature is higher than 100° C., the side reaction is likely to arise and thus the yield and purity may decrease.

The dithienyl sulfide sulfonium salt thus obtained can be isolated by a method of filtering a solid precipitated after the completion of the reaction, or a method of extracting with an organic solvent such as monochlorobenzene, ethyl acetate or dichloromethane and distilling off the organic solvent. The dithienyl sulfide sulfonium salt can be optionally purified by a conventional method such as recrystallization from a solvent such as monochlorobenzene, toluene, ethyl acetate, acetone, methanol, ethanol, isopropanol, n-heptane, or water, an activated carbon treatment, or column purification.

The phenylthiothiophene sulfonium salt according to the third aspect of the present invention is a compound represented by the following formula (C1).

[Chemical Formula 10]

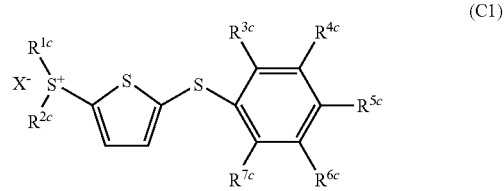

(C1)

In the formula (C1), $R^{1c}$ and $R^{2c}$ each independently represents an optionally substituted monocyclic carbon ring group, an optionally substituted condensed polycyclic carbon ring group or an optionally substituted monocyclic heterocyclic group, $R^{3c}$ to $R^{7c}$ each independently represents a hydrogen atom, an alkyl group having 1 to 10 carbon atoms, an alkoxy group having 1 to 4 carbon atoms, an acyl group or a hydroxyl group, and $X^-$ represents an inorganic acid ion or an organic acid ion.

Examples of the optionally substituted monocyclic carbon ring group represented by $R^{1c}$ and $R^{2c}$ include a phenyl group and a phenyl group having a substituent.

Examples of the optionally substituted condensed polycyclic carbon ring group include a naphthyl group and a naphthyl group having a substituent.

Examples of the optionally substituted monocyclic heterocyclic group include a thienyl group and a thienyl group having a substituent.

Examples of the substituent include a hydroxyl group, an acetoxy group, a phenyl group, an alkyl group having 1 to 10 carbon atoms, an alkoxy group having 1 to 4 carbon atoms, an alkylthio group having 1 to 4 carbon atoms, and a halogen atom.

Examples of the alkyl group having 1 to 10 carbon atoms include a methyl group, an ethyl group, a propyl group, a butyl group, a pentyl group, a hexyl group, an octyl group, and a decyl group.

Examples of the alkoxy group having 1 to 4 carbon atoms include a methoxy group, an ethoxy group, a propoxy group, a butoxy group, and a methoxyethoxy group Examples of the alkylthio group having 1 to 4 carbon atoms include a methylthio group, an ethylthio group, a propylthio group, and a butylthio group.

Examples of the halogen atom include a fluorine atom, a chlorine atom, a bromine atom, and an iodine atom.

As the group represented by $R^{1c}$ and $R^{2c}$ in the formula (C1), an optionally substituted monocyclic carbon ring group is preferably used, and a phenyl group and a phenyl group having a substituent are more preferably used. As the substituent in the phenyl group having a substituent, a methyl group, an ethyl group, an n-propyl group, an isopropyl group, an n-butyl group, a tert-butyl group, a methoxy group, an ethoxy group, an n-propoxy group, an isopropoxy group, an n-butoxy group, an isobutoxy group, a sec-butoxy group, a tert-butoxy group, a methylthio group and a fluorine atom are preferably used, and a methyl group, an ethyl group, an n-propyl group, an isopropyl group, an n-butyl group, a methoxy group, an ethoxy group, an n-propoxy group, an isopropoxy group and an n-butoxy group are more preferably used.

The optionally substituted monocyclic carbon ring group, the optionally substituted condensed polycyclic carbon ring group and the optionally substituted monocyclic heterocyclic group may have one substituent or may have a plurality of substituents. In the case of having a plurality of substituents, the substituent may be the same or different.

Examples of the alkyl group having 1 to 10 carbon atoms represented by $R^{3c}$ to $R^{7c}$ in the formula (C1) include a methyl group, an ethyl group, a propyl group, a butyl group, a pentyl group, a hexyl group, an octyl group, and a decyl group.

Examples of the alkoxy group having 1 to 4 carbon atoms represented by $R^{3c}$ to $R^{7c}$ include a methoxy group, an ethoxy group, a propoxy group, and a butoxy group.

Examples of the acyl group represented by $R^{3c}$ to $R^{7c}$ include an acetyl group, a formyl group, and a benzoyl group.

Examples of the group represented by $R^{3c}$ to $R^{7c}$ in the formula (C1) include a hydrogen atom, a methyl group, an ethyl group, an n-propyl group, an n-butyl group, a methoxy group, an ethoxy group, an n-propoxy group, an n-butoxy group, and an acetyl group.

Examples of the inorganic acid ion represented by $X^-$ in the formula (C1) include, but are not particularly limited to, a hexafluoroantimonic acid ion, a hexafluoroarsenic acid ion, a hexafluorophosphoric acid ion, a pentafluorohydroxoantimonic acid ion, a tetrafluoroboric acid ion, a tetrakis(pentafluorophenyl)boric acid ion, a tetrakis(trifluoromethylphenyl)boric acid ion, a trifluoro(pentafluorophenyl)boric acid ion, a tetrakis(difluorophenyl)boric acid ion, and a difluorobis(pentafluorophenyl)boric acid ion.

Examples of the organic acid ion represented by $X^-$ in the formula (C1) include, but are not particularly limited to, a methanesulfonic acid ion, an ethanesulfonic acid ion, a propanesulfonic acid ion, a butanesulfonic acid ion, an octanesulfonic acid ion, a trifluoromethanesulfonic acid ion, a perfluorobutanesulfonic acid ion, a perfluorohexanesulfonic acid ion, a benzenesulfonic acid ion, a benzene-1,3-disulfonic acid ion, a p-toluenesulfonic acid ion, an anthraquinone-1-sulfonic acid ion, an anthraquinone-2-sulfonic acid ion, an anthraquinone-1,5-disulfonic acid ion, a methanecarboxylic acid ion, an ethanecarboxylic acid ion, a propanecarboxylic acid ion, a butanecarboxylic acid ion, an octanecarboxylic acid ion, a trifluoromethanecarboxylic acid ion, a benzenecarboxylic acid ion, a p-toluenecarboxylic acid ion, a bis(trifluoromethanesulfonyl)imide ion, and a tris(trifluoromethanesulfonyl)methide ion.

Of these acid ions, a hexafluorophosphoric acid ion, a tetrakis(pentafluorophenyl)boric acid ion, a trifluoromethanesulfonic acid ion and a perfluorobutanesulfonic acid ion are preferably used in view of acid strength and safety of an acid generated when the phenylthiothiophene sulfonium salt is used as the photoacid generator.

Specific examples of the phenylthiothiophene sulfonium salt according to the second aspect of the present invention include diphenyl (5-phenylthio-thiophen-2-yl)sulfonium perfluorobutanesulfonate, diphenyl(5-phenylthio-thiophen-2-yl)sulfonium trifluoromethanesulfonate, diphenyl(5-phenylthio-thiophen-2-yl)sulfonium hexafluorophosphate, diphenyl(5-phenylthio-thiophen-2-yl)sulfonium tetrakis(pentafluorophenyl)borate, bis(4-methylphenyl) (5-phenylthio-thiophen-2-yl)sulfonium perfluorobutanesulfonate, bis(4-methylphenyl) (5-phenylthio-thiophen-2-yl)sulfonium trifluoromethanesulfonate, bis(4-methylphenyl) (5-phenylthio-thiophen-2-yl)sulfonium hexafluorophosphate, bis (4-methylphenyl) (5-phenylthio-thiophen-2-yl)sulfonium tetrakis(pentafluorophenyl)borate, bis(4-methoxyphenyl) (5-phenylthio-thiophen-2-yl)sulfonium perfluorobutanesulfonate, bis(4-methoxyphenyl) (5-phenylthio-thiophen-2-yl)sulfonium trifluoromethanesulfonate, bis(4-methoxyphenyl) (5-phenylthio-thiophen-2-yl)sulfonium hexafluorophosphate, bis(4-methoxyphenyl) (5-phenylthio-thiophen-2-yl)sulfonium tetrakis(pentafluorophenyl)borate, diphenyl[5-(4-methyl-phenylthio)-thiophen-2-yl]sulfonium perfluorobutanesulfonate, diphenyl[5-(4-methyl-phenylthio)-thiophen-2-yl]sulfonium trifluoromethanesulfonate, diphenyl[5-(4-methyl-phenylthio)-thiophen-2-yl]sulfonium hexafluorophosphate, diphenyl[5-(4-methyl-phenylthio)-thiophen-2-yl]sulfonium tetrakis(pentafluorophenyl)borate, bis(4-methylphenyl)[5-(4-methyl-phenylthio)-thiophen-2-yl]sulfonium perfluorobutanesulfonate, bis(4-methylphenyl)[5-(4-methyl-phenylthio)-thiophen-2-yl]sulfonium trifluoromethanesulfonate, bis(4-methylphenyl)[5-(4-methyl-phenylthio)-thiophen-2-yl]sulfonium hexafluorophosphate, bis(4-methylphenyl)[5-(4-methyl-phenylthio)-thiophen-2-yl]sulfonium tetrakis(pentafluorophenyl)borate, bis(4-methoxyphenyl)[5-(4-methyl-phenylthio)-thiophen-2-yl]sulfonium perfluorobutanesulfonate, bis(4-methoxyphenyl)[5-(4-methyl-phenylthio)-thiophen-2-yl]sulfonium trifluoromethanesulfonate, bis(4-methoxyphenyl)[5-(4-methyl-phenylthio)-thiophen-2-yl]sulfonium hexafluorophosphate, bis(4-methoxyphenyl)[5-(4-methyl-phenylthio)-thiophen-2-yl]sulfonium tetrakis(pentafluorophenyl)borate, diphenyl[5-(4-methoxy-phenylthio)-thiophen-2-yl]sulfonium perfluorobutanesulfonate, diphenyl[5-(4-methoxy-phenyl)thio-thiophen-2-yl]sulfonium trifluoromethanesulfonate, diphenyl[5-(4-methoxy-phenylthio)-thiophen-2-yl]sulfonium hexafluorophosphate, diphenyl[5-(4-methoxy-phenylthio)-thiophen-2-yl]sulfonium tetrakis(pentafluorophenyl)borate, bis(4-methylphenyl)[5-(4-methoxy-phenylthio)-thiophen-2-yl]sulfonium perfluorobutanesulfonate, bis(4-methylphenyl)[5-(4-methoxy-phenylthio)-thiophen-2-yl]sulfonium trifluoromethanesulfonate, bis(4-methylphenyl)[5-(4-methoxy-phenylthio)-thiophen-2-yl]sulfonium hexafluorophosphate, bis(4-methylphenyl)[5-(4-methoxy-phenylthio)-thiophen-2-yl]sulfonium tetrakis(pentafluorophenyl)borate, bis(4-methoxyphenyl)[5-(4-methoxy-phenylthio)-thiophen-2-yl]sulfonium perfluorobutanesulfonate, bis(4-methoxyphenyl)[5-(4-methoxy-phenylthio)-thiophen-2-yl]sulfonium trifluoromethanesulfonate, bis(4-methoxyphenyl)[5-(4-methoxy-phenylthio)-thiophen-2-yl]sulfonium hexafluorophosphate, bis(4-methoxyphenyl)[5-(4-methoxy-phenylthio)-thiophen-2-yl]sulfonium tetrakis(pentafluorophenyl)borate, diphenyl[5-(4-acetyl-phenylthio)-thiophen-2-yl]sulfonium perfluorobutanesulfonate, diphenyl[5-(4-acetyl-phenylthio)-thiophen-2-yl]sulfonium trifluoromethanesulfonate, diphenyl[5-(4-acetyl-phenylthio)-thiophen-2-yl]sulfonium hexafluorophosphate, diphenyl[5-(4-acetyl-phenylthio)-thiophen-2-yl]sulfonium tetrakis(pentafluorophenyl)borate, bis(4-methylphenyl)[5-(4-acetyl-phenylthio)-thiophen-2-yl]sulfonium perfluorobutanesulfonate, bis(4-methylphenyl)[5-(4-acetyl-phenylthio)-thiophen-2-yl]sulfonium trifluoromethanesulfonate, bis(4-methylphenyl)[5-(4-acetyl-phenylthio)-thiophen-2-yl]sulfonium hexafluorophosphate, bis(4-methylphenyl)[5-(4-acetyl-phenylthio)-thiophen-2-yl]sulfonium tetrakis(pentafluorophenyl)borate, bis(4-methoxyphenyl)[5-(4-acetyl-phenylthio)-thiophen-2-yl]sulfonium perfluorobutanesulfonate, bis(4-methoxyphenyl)[5-(4-acetyl-phenylthio)-thiophen-2-yl]sulfonium trifluoromethanesulfonate, bis(4-methoxyphenyl)[5-(4-acetyl-phenylthio)-thiophen-2-yl]sulfonium hexafluorophosphate, and bis(4-methoxyphenyl)[5-(4-acetyl-phenylthio)-thiophen-2-yl]sulfonium tetrakis(pentafluorophenyl)borate.

The phenylthiothiophene sulfonium salt represented by the formula (C1) can be produced, for example, by condensing sulfoxide represented by the following formula (C2):

[Chemical Formula 11]

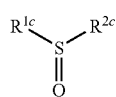

(C2)

wherein $R^{1c}$ and $R^{2c}$ each represent the same group as that for $R^{1c}$ and $R^{2c}$ in the formula (C1), with a phenylthiothiophene compound represented by the following formula (C3):

[Chemical Formula 12]

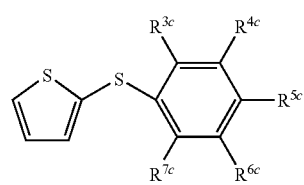

(C3)

wherein $R^{3c}$ to $R^{7c}$ each represents the same group as that for $R^{3c}$ to $R^{7c}$ in the formula (C1), in the presence of a condensing agent and a strong acid, and reacting the condensation reaction product with an alkali metal salt of an inorganic acid corresponding to the inorganic acid ion, or an alkali metal salt of an organic acid corresponding to the organic acid ion.

Specific examples of the sulfoxide represented by the formula (C2) include diphenyl sulfoxide, bis(4-methylphenyl)sulfoxide, bis(4-ethylphenyl)sulfoxide, bis(4-n-propylphenyl)sulfoxide, bis(4-isopropylphenyl) sulfoxide, bis(4-n-butylphenyl)sulfoxide, bis(4-tert-butylphenyl)sulfoxide, bis(4-phenylphenyl)sulfoxide, bis(4-methoxyphenyl)sulfoxide, bis(4-ethoxyphenyl) sulfoxide, bis(4-n-propoxyphenyl)sulfoxide, bis(4-isopropoxyphenyl)sulfoxide, bis(4-n-butoxyphenyl) sulfoxide, bis(4-isobutoxyphenyl)sulfoxide, bis(4-sec-butoxyphenyl)sulfoxide, bis(4-tert-butoxyphenyl) sulfoxide, bis(4-methylthiophenyl)sulfoxide, bis(4-ethylthiophenyl) sulfoxide, bis(4-n-propylthiophenyl) sulfoxide, bis(4-isopropylthiophenyl)sulfoxide, bis(4-n-butylthiophenyl) sulfoxide, bis(4-tert-butylthiophenyl) sulfoxide, bis(4-hydroxyphenyl)sulfoxide, bis(4-acetoxyphenyl)sulfoxide, bis(4-fluorophenyl)sulfoxide, bis(4-chlorophenyl)sulfoxide, bis(4-bromophenyl)sulfoxide, bis(4-iodophenyl)sulfoxide, bis(2,4-dimethylphenyl)sulfoxide, bis(3,4-dimethylphenyl)sulfoxide, bis(2,4,6-trimethylphenyl)sulfoxide, di-(2-thienyl)sulfoxide, and di-(2-naphthyl)sulfoxide.

Of these sulfoxides, diphenyl sulfoxide, bis(4-methylphenyl)sulfoxide, bis(4-ethylphenyl)sulfoxide, bis(4-n-propylphenyl)sulfoxide, bis(4-isopropylphenyl)sulfoxide, bis(4-n-butylphenyl)sulfoxide, bis(4-methoxyphenyl)sulfoxide, bis(4-ethoxyphenyl)sulfoxide, bis(4-n-propoxyphenyl) sulfoxide, bis(4-isopropoxyphenyl)sulfoxide, bis(4-n-butoxyphenyl)sulfoxide, bis(4-methylthiophenyl)sulfoxide, bis(4-fluorophenyl)sulfoxide, and bis(2,4-dimethylphenyl)sulfoxide are preferably used.

A commercially available sulfoxide may be used as it is, or an appropriately produced sulfoxide may be used.

There is no particular limitation on a method for producing the sulfoxide. When the sulfoxide is bis(4-methylphenyl)sulfoxide in which both $R^{1c}$ and $R^{2c}$ in the formula (C2) are 4-methylphenyl groups, the sulfoxide can be produced by a known method such as a method of reacting toluene with thionyl chloride in the presence of trifluoromethanesulfonic acid (Synlett., 1999, 1397). When sulfoxide is 4-methylphenyl-(2,4-dimethylphenyl)sulfoxide in which $R^{1c}$ in the formula (C2) is a 4-methylphenyl group and $R^{2c}$ is a 2,4-dimethylphenyl group, the sulfoxide can be produced by a known method such as a method of reacting m-xylene with p-toluenesulfinyl chloride in the presence of aluminum chloride (J. Org. Chem., 1974, 39, 1203).

Specific examples of the phenylthiothiophene compound represented by the formula (C3) include 2-(phenylthio)thiophene, 2-(4-methyl-phenylthio)thiophene, 2-(4-ethyl-phenylthio)thiophene, 2-(4-n-propyl-phenylthio)thiophene, 2-(4-isopropyl-phenylthio)thiophene, 2-(4-n-butyl-phenylthio)thiophene, 2-(4-isobutyl-phenylthio)thiophene, 2-(4-methoxy-phenylthio)thiophene, 2-(4-ethoxy-phenylthio)thiophene, 2-(4-n-propoxy-phenylthio)thiophene, 2-(4-isopropoxy-phenylthio)thiophene, 2-(4-n-butoxy-phenylthio)thiophene, 2-(4-isobutoxy-phenylthio)thiophene, 2-(4-acetyl-phenylthio)thiophene, 2-(4-benzoyl-phenylthio)thiophene, and 2-(4-hydroxy-phenylthio)thiophene.

Of these phenylthiothiophene compounds, 2-(phenylthio)thiophene, 2-(4-methyl-phenylthio)thiophene, 2-(4-ethyl-phenylthio)thiophene, 2-(4-n-propyl-phenylthio)thiophene, 2-(4-n-butyl-phenylthio)thiophene, 2-(4-methoxy-phenylthio)thiophene, 2-(4-ethoxy-phenylthio)-thiophene, 2-(4- n-propoxy-phenylthio)-thiophene, 2-(4-n-butoxy-phenylthio)thiophene, and 2-(4-acetyl-phenylthio)thiophene are preferably used.

The phenylthiothiophene compound can be produced by a known method. Specifically, the phenylthiothiophene compound can be produced, for example, by reacting 2-iodothiophene with thiophenol in the presence of copper (I) iodide and a neocuproin catalyst (Org. Lett., 2002, 4, 2803) when the phenylthiothiophene compound is 2-(phenylthio)thiophene in which all of $R^{3c}$ to $R^{7c}$ in the formula (C3) are hydrogen atoms. Similarly, when the phenylthiothiophene compound is 2-(4-methyl-phenylthio)thiophene in which $R^{bc}$ in the formula (C3) is a methyl group and all of $R^{3c}$, $R^{4c}$, $R^{6c}$ and $R^{7c}$ are hydrogen atoms, it can be produced by a method of reacting 2-iodothiophene with 4-methyl-thiophenol in the presence of copper (I) iodide and a neocuproin catalyst.

The amount of sulfoxide used is not particularly limited and is preferably from 0.6 to 2.0 mol, more preferably from 0.8 to 1.8 mol, and particularly preferably from 0.9 to 1.6 mol, based on 1 mol of the phenylthiothiophene compound represented by the formula (C3) in view of an improvement in yield and economical efficiency.

Examples of the condensing agent include, but are not particularly limited to, acetic anhydride, trifluoroacetic anhydride, concentrated sulfuric acid, diphosphorus pentaoxide, and polyphosphoric acid. Of these condensing agents, acetic anhydride, concentrated sulfuric acid and diphosphorus pentaoxide are preferably used. These condensing agents may be used alone, or two or more kinds thereof may be used in combination.

The amount of the condensing agent used is not particularly limited and is preferably from 1 to 40 mol, and more preferably from 1 to 30 mol, based on 1 mol of the phenylthiothiophene compound. When the amount of the condensing agent is less than 1 mol, the yield may decrease. In contrast, when the amount of the condensing agent is more than 40 mol, it is not economical because the effect corresponding to the amount of use is not exerted.

Examples of the strong acid include, but are not particularly limited to, methanesulfonic acid, ethanesulfonic acid and trifluoromethanesulfonic acid. Of these strong acids, methanesulfonic acid is preferably used. These strong acids may be used alone, or two or more kinds thereof may be used in combination.

The amount of the strong acid used is not particularly limited and is preferably from 1 to 50 mol, and more preferably from 2 to 30 mol, based on 1 mol of the phenylthiothiophene compound. When the amount of the strong acid is less than 1 mol, the yield may decrease. In contrast, when the amount of the strong acid is more than 50 mol, it is not economical because the effect corresponding to the amount of use is not exerted and volume efficiency deteriorates.

In the reaction of condensing sulfoxide with a phenylthiothiophene compound in the presence of a condensing agent and a strong acid, a reaction solvent is not necessarily required. For the purpose of improving stirring efficiency, a solvent such as sulfolane, dichloromethane or chloroform may be used as the reaction solvent. The amount of the reaction solvent is preferably from 30 to 3,000 parts by weight, and more preferably from 50 to 2,000 parts by weight, based on 100 parts by weight of the dithienyl sulfide compound.

There is no particular limitation on the operation in the condensation reaction. For example, there is exemplified a method of adding dropwise a predetermined amount of the strong acid while mixing and stirring a predetermined amount of the sulfoxide, a phenylthiothiophene compound, a condensing agent and, if necessary, the reaction solvent.

The reaction temperature is preferably from −20 to 100° C., and more preferably from −10 to 80° C. When the reaction temperature is lower than −20° C., the reaction may require a long time because the reaction rate decreases. In contrast, when the reaction temperature is higher than 100° C., the side reaction is likely to arise and thus the yield and purity may decrease. The reaction time varies depending on the reaction temperature and is usually from 0.5 to 48 hours, and preferably from 1 to 24 hours.

The phenylthiothiophene sulfonium salt represented by the formula (C1) can be produced by condensing sulfoxide with a phenylthiothiophene compound, and reacting the condensation reaction product with an alkali metal salt of the inorganic acid or an alkali metal salt of the organic acid.

Specific examples of the alkali metal salt of the inorganic acid include sodium hexafluoroantimonate, potassium hexafluoroantimonate, sodium hexafluoroarsenate, potassium hexafluoroarsenate, sodium hexafluorophosphate, potassium hexafluorophosphate, sodium pentafluorohydroxoantimonate, potassium pentafluorohydroxoantimonate, sodium tetrafluoroborate, potassium tetrafluoroborate, lithium tetrakis(pentafluorophenyl)borate, sodium tetrakis(pentafluorophenyl)borate, potassium tetrakis(pentafluorophenyl)borate, lithium tetrakis(trifluoromethylphenyl)borate, sodium tetrakis(trifluoromethylphenyl)borate, potassium tetrakis(trifluoromethylphenyl)borate, lithium trifluoro(pentafluorophenyl)borate, sodium trifluoro(pentafluorophenyl)borate, potassium trifluoro(pentafluorophenyl)borate, lithium tetrakis(difluorophenyl)borate, sodium tetrakis(difluorophenyl)borate, potassium tetrakis(difluorophenyl)borate, lithium difluorobis(pentafluorophenyl)borate, sodium difluorobis(pentafluorophenyl)borate, and potassium difluorobis(pentafluorophenyl)borate.

Specific examples of the alkali metal salt of the organic acid include sodium methanesulfonate, potassium methanesulfonate, sodium ethanesulfonate, potassium ethanesulfonate, sodium propanesulfonate, potassium propanesulfonate, sodium butanesulfonate, potassium butanesulfonate, sodium octanesulfonate, potassium octanesulfonate, sodium trifluoromethanesulfonate, potassium trifluoromethanesulfonate, sodium perfluorobutanesulfonate, potassium perfluorobutanesulfonate, sodium benzenesulfonate, potassium benzenesulfonate, sodium benzene-1,3-disulfonate, potassium benzene-1,3-disulfonate, sodium p-toluenesulfonate, potassium p-toluenesulfonate, sodium anthraquinone-1-sulfonate, potassium anthraquinone-1-sulfonate, sodium anthraquinone-2-sulfonate, potassium anthraquinone-2-sulfonate, sodium anthraquinone-1,5-disulfonate, potassium anthraquinone-1,5-disulfonate, sodium methane carboxylate, potassium methane carboxylate, sodium ethane carboxylate, potassium ethane carboxylate, sodium propane carboxylate, potassium propane carboxylate, sodium butane carboxylate, potassium butane carboxylate, sodium octane carboxylate, potassium octane carboxylate, sodium trifluoromethane carboxylate, potassium trifluoromethane carboxylate, sodium benzene carboxylate, potassium benzene carboxylate, sodium p-toluene carboxylate, potassium p-toluene carboxylate, lithium bis(trifluoromethanesulfonyl)imide, and lithium tris(trifluoromethanesulfonyl)methide.

Of these alkali metal salts, sodium hexafluorophosphate, potassium hexafluorophosphate, lithium tetrakis(pentafluorophenyl)borate, sodium tetrakis(pentafluorophenyl)borate, potassium tetrakis(pentafluorophenyl)borate, sodium trifluoromethanesulfonate, potassium trifluoromethanesulfonate, sodium perfluorobutanesulfonate and potassium perfluorobutanesulfonate are preferred in view of acid strength and safety of an acid generated when the phenylthiothiophene sulfonium salt is used as the photoacid generator.

The amount of the alkali metal salt used is not particularly limited and is preferably from 0.6 to 1.8 mol, and more preferably from 0.8 to 1.6 mol, based on 1 mol of the phenylthiothiophene compound. When the amount of the alkali metal salt is less than 0.6 mol, the yield may decrease. In contrast, when the amount of the alkali metal salt is more than 1.8 mol, it is not economical because the effect corresponding to the amount of use is not exerted. Both the alkali metal salt of the inorganic and the alkali metal salt of the organic acid can be used as an aqueous solution. The concentration in the case of using as the aqueous solution is preferably from 1 to 80% by weight, and more preferably from 3 to 50% by weight.

There is no particular limitation on the operation in the reaction of the condensation reaction product with the alkali metal salt. Examples of the method used in the operation in the reaction include a method of adding a predetermined amount of the alkali metal salt to the reaction solution after the condensation reaction, a method of adding the reaction solution after the condensation reaction to a predetermined amount of the alkali metal salt, a method of adding the reaction solution after the condensation reaction to a predetermined amount of water to form an aqueous solution of the condensation reaction product and adding an alkali metal salt, and a method of adding the reaction solution after the condensation reaction to a predetermined amount of water to form an aqueous solution of the condensation reaction product and adding the aqueous solution to an alkali metal salt. In the case of these operations, an organic solvent such as monochlorobenzene, ethyl acetate or dichloromethane may exist.

The reaction temperature is preferably from −10 to 100° C., and more preferably from 0 to 80° C. When the reaction temperature is lower than −10° C., the reaction may require a long time because the reaction rate decreases. In contrast, when the reaction temperature is higher than 100° C., the side reaction is likely to arise and thus the yield and purity may decrease.

The phenylthiothiophene sulfonium salt thus obtained can be isolated by a method of filtering a solid precipitated after the completion of the reaction, or a method of extracting with an organic solvent such as monochlorobenzene, ethyl acetate or dichloromethane and distilling off the organic solvent. The dithienyl sulfide sulfonium salt can be optionally purified by a conventional method such as recrystallization from a solvent such as monochlorobenzene, toluene, ethyl acetate, acetone, methanol, ethanol, isopropanol, n-heptane, or water, an activated carbon treatment, or column purification.

The photoacid generator according to the present invention contains a dithienyl sulfide disulfonium salt represented by the formula (A1). In the photoacid generator, the dithienyl sulfide disulfonium salts may be used alone, or two or more kinds thereof may be used in combination.

The photoacid generator according to the present invention contains a dithienyl sulfide sulfonium salt represented by the formula (B1). In the photoacid generator, the dithienyl sulfide sulfonium salts may be used alone, or two or more kinds thereof may be used in combination.

The photoacid generator according to the present invention contains a phenylthiothiophene sulfonium salt represented by the formula (C1). In the photoacid generator, the phenylthiothiophene sulfonium salts may be used alone, or two or more kinds thereof may be used in combination.

The photoreactive composition according to the present invention contains the photoacid generator and an acid reactive compound.

In the present invention, the acid reactive compound is a compound in which a chemical reaction such as polymerization or decomposition arises in the presence of an acid generated by a photoacid generator irradiated with light having a specific wavelength. Examples of the acid reactive compound include cation polymerizable compounds such as a cation polymerizable monomer, a cation polymerizable oligomer, and a cation polymerizable polymer; and various resist materials in which an ester bond or an ether bond in a polymer is decomposed, or a polymer side chain is cross-linked.

Specific examples of the cation polymerizable compound include monofunctional glycidyl ether compounds such as allyl glycidyl ether, butyl glycidyl ether, phenyl glycidyl ether, 2-ethylhexyl glycidyl ether, and 2-methyloctyl glycidyl ether;

polyfunctional glycidyl ether compounds such as 1,6-hexanediol diglycidyl ether, trimethylolpropane triglycidyl ether, ethylene glycol diglycidyl ether, and polypropylene glycol diglycidyl ether;

glycidyl ester compounds such as glycidyl (meth)acrylate, diglycidyl diphthalate, and diglycidyl tetrahydrophthalate;

compounds prepared by glycidyl etherification of bisphenol A, bisphenol F, brominated bisphenol A, biphenol, resorcin, a bisphenol novolak resin, a phenol novolak resin, and a cresol novolak resin;

alicyclic epoxy compounds such as 3,4-epoxycyclohexylmethyl-3,4-epoxycyclohexane carboxylate, 3,4-epoxycyclohexylethyl-3,4-epoxycyclohexane carboxylate, vinylcyclohexene dioxide, allylcyclohexene dioxide, 3,4-epoxy-4-methylcyclohexyl-2-propylene oxide, and bis(3,4-epoxycyclohexyl)ether;

hydroxyalkyl (meth)acrylates such as 2-hydroxyethyl (meth)acrylate and 2-hydroxybutyl (meth)acrylate;

vinyl compounds such as vinyl acetate, acrylonitrile, methacrylonitrile, vinylidene chloride, vinyl chloride, styrene, sodium styrenesulfonate, 2-methylstyrene, vinyltoluene, tert-butylstyrene, chlorostyrene, vinylanisole, vinylnaphthalene, ethylene, propylene, isopropylene, butadiene, chloroprene, vinylketone, and N-vinyl pyrrolidone;

vinylether compounds such as ethylene glycol vinyl ether, ethylene glycol divinyl ether, diethylene glycol vinyl ether, diethylene glycol divinyl ether, and 1,4-cyclohexane dimethanol divinyl ether;

isocyanate compounds such as tolylene diisocyanate, xylylene diisocyanate, diphenylmethane diisocyanate, naphthylene diisocyanate, lysine diisocyanate methyl ester, trimethylhexamethylene diisocyanate, dimmer acid diisocyanate, hexamethylene diisocyanate, 4,4-bis(isocyanatocyclohexyl)methane, and isophorone diisocyanate;

oxetane compounds such as trimethylene oxide, 3-ethyl-3-hydroxymethyloxetane, 3,3-dimethyloxetane, 3,3-dichloromethyloxetane, 3-ethyl-3-phenoxymethyloxetane, bis(3-ethyl-3-oxetanylmethyl)ether, 1,4-bis{[(3-ethyl-3-oxetanyl)methoxy]methyl}benzene, tri{(3-ethyl-3-oxetanylmethoxy)methyl]benzene, bis{(3-ethyl-3-oxetanylmethoxy)methylphenyl]ether, (3-ethyl-3-oxetanylmethoxy)oligodimethylsiloxane, spiro[bicyclo[2.2.2]octane-2,3'-oxetane], spiro[7-oxabicyclo[2.2.1]heptane-2,3'-oxetane], 5-methyl-2-oxaspiro[3.5]nonane, and spiro[3-methylbicyclo[2.2.1]heptane-2,3'-oxetane]; and episulfide compounds such as 2,3-epithiopropylthiobenzene, 2,3-epithiopropylthiobutane, 2,3-epithiopropylthiohexane, 2,3-epithiopropylthiobenzene, 2,3-epithiopropyloxybenzene, 2,3-epithiopropyloxybutane, 2,3-epithiopropyloxyhexane, 2,3-epithiopropyl(meth)acrylate, bis[4-(2,3-epithiopropylthio)phenyl]sulfide, bis[4-(2,3-epithiopropylthio)phenyl]ether, and bis[4-(2,3-epithiopropylthio)phenyl]methane. The "(meth)acrylate" means acrylate and methacrylate.

Of these cation polymerizable compounds, monofunctional glycidyl ether compounds, polyfunctional glycidyl ether compounds, glycidyl ester compounds, alycyclic epoxy compounds, vinyl ether compounds and oxetane compounds are preferably used in view of effective utilization of high acid generating ability of the photoacid generator.

In the present invention, the acid reactive compounds may be used alone, or two or more kind thereof may be used in combination.

In the photoreactive composition according to the present invention, the amount of the photoacid generator used is not particularly limited and is preferably from 0.01 to 10 parts by weight, and more preferably from 0.1 to 5 parts by weight, based on 100 parts by weight of the acid reactive compound. When the amount of the photoacid generator is less than 0.01 part by weight, the effect of the acid may become insufficient. In contrast, when the amount of the photoacid generator is more than 10 parts by weight, it is not economical because the effect corresponding to the amount of use is not exerted.

The photoreactive composition according to the present invention may contain an organic solvent as the solvent. Specific examples of the organic solvent include ethyl acetate, butyl acetate, methyl cellosolve, ethyl cellosolve, methyl cellosolve acetate, ethyl cellosolve acetate, ethylene glycol dimethyl ether, ethylene glycol diethyl ether, diethylene glycol dimethyl ether, diethylene glycol diethyl ether, propylene carbonate, propylene glycol-1-monomethyl ether-2-acetate, ethyl lactate, γ-butyrolactone, and isopropyl alcohol.

The amount of the organic solvent used is preferably from 0.1 to 100 parts by weight, and more preferably from 1 to 50 parts by weight, based on 100 parts by weight of the acid reactive compound.

The photoreactive composition according to the present invention may contain polymerization inhibitors such as 2,6-di-tert-butyl-p-cresol, hydroquinone, and p-methoxyphenol; dyes such as eosin, methylene blue, and malachite green; sensitizers such as 2,4-diethylthioxanethone, 2-ethylanthraquinone, 9,10-diethoxyanthracene, 9,10-dipropoxyanthracene, and 9,10-dibutoxyanthracene; and photoacid generators other than the photoacid generator according to the present invention, such as benzyl dimethyl ketal and benzoin isopropyl ether.

The amount of the polymerization inhibitor used is preferably from 0.001 to 5 parts by weight, and more preferably from 0.005 to 1 part by weight, based on 100 parts by weight of the acid reactive compound. Each of the amounts of the dye, the sensitizer and the photoacid generator other than the photoacid generator according to the present invention used is preferably from 0.01 to 10 parts by weight, and more preferably from 0.01 to 5 parts by weight, based on 100 parts by weight of the acid reactive compound.

The photoreactive composition according to the present invention can be produced, for example, by mixing and stirring a predetermined amount of the photoacid generator and acid reactive compound and, if necessary, an organic solvent, a polymerization inhibitor, a dye, a sensitizer and a photoacid generator other than the photoacid generator according to the present invention.

The mixing and stirring temperature is not particularly limited and is usually from 0 to 100° C., and preferably from 10 to 60° C. The mixing and stirring time is preferably from 0.1 to 24 hours, and more preferably from 0.1 to 6 hours.

The photoreactive composition thus obtained can be reacted by irradiation with near ultraviolet light as it is, or in the state where optionally used organic solvent is vaporized or remained.

Specifically, when a cation polymerizable monomer is used as the acid reactive compound, a photoreactive composition containing the acid reactive compound is coated on a smooth aluminum or glass plate in a thickness of 0.1 to 200 µm and irradiating with near ultraviolet light, thus making it possible to obtain a thin film of a polymerization-cured resin.

Examples of a light source of near ultraviolet light include a high-pressure mercury lamp, a low-pressure mercury lamp, a metal halide lamp, a xenon lamp, a germicidal lamp, and laser beam. The irradiation time varies depending on the light source and the kind and amount of photoacid generator and cannot be unconditionally defined, but is preferably from 0.1 second to 10 hours, and more preferably from 0.5 second to 1 hour.

EXAMPLES

The present invention will be described in more detail by way of Examples and Comparative Examples, but the present invention is not limited to these Examples.

Example A1

In a 100 mL four-necked flask equipped with a stirrer, a thermometer and a condenser, 5.2 g (0.02 mol) of bis(4-methoxyphenyl)sulfoxide, 2.0 g (0.01 mol) of 2,2'-dithienyl sulfide and 10.2 g (0.1 mol) of acetic anhydride were charged and 7.7 g (0.08 mol) of methanesulfonic acid was added dropwise over 1 hour while maintaining the inner temperature at 0 to 10° C. After completion of the dropwise addition, stirring was conducted for 2 hours while maintaining at the same temperature to obtain a reaction solution as a condensation reaction product.

In a 200 mL four-necked flask equipped with a stirrer, a thermometer and a condenser, 3.7 g (0.02 mol) of potassium hexafluorophosphate, 40 g of water and 30 g of monochlorobenzene were charged and the entire amount of the reaction solution was added dropwise over 30 minutes while maintaining the inner temperature at 30 to 50° C. After stirring at 40 to 50° C. for 30 minutes, the monochlorobenzene layer was separated and monochlorobenzene was distilled off to obtain 9.3 g of a brown concentrate.

This concentrate was purified by silica gel column chromatography to obtain 7.9 g (0.008 mol) of (thiodi-5,2-thienylene)bis[bis(4-methoxyphenyl)sulfonium]bishexafluorophosphate as a pale yellow solid. As a result of the measurement by high performance liquid chromatograph, purity of the resultant (thiodi-5,2-thienylene)bis[bis(4-methoxyphenyl)sulfonium]bishexafluorophosphate was 98.6%. Also, the yield to 2,2'-dithienyl sulfide was 80%.

It was confirmed by analytical results shown below that the resultant pale yellow solid is (thiodi-5,2-thienylene)bis[bis(4-methoxyphenyl)sulfonium]bishexafluorophosphate in which all $R^{1a}$, $R^{2a}$, $R^{3a}$ and $R^{4a}$ in the formula (A1) are 4-methoxyphenyl groups and $X^-$ is a hexafluorophosphoric acid ion. The molar extinction coefficient was determined by measuring using a spectrophotometer for ultraviolet and visible region (manufactured by Shimadzu Corporation under the trade name of UV-2500(PC)S).

Elemental analysis: C; 44.1%, H; 3.3%, F; 23.5%, O; 6.4%, S; 16.6% (theoretical value: C; 44.17%, H; 3.29%, F; 23.29%, O; 6.54%, S; 16.38%)

$^1$H-Nuclear magnetic resonance spectrum (400 MHz, $CD_2Cl_2$) δ (ppm): 3.93(s, 12H), 7.18-7.24(m, 8H), 7.45(d, 2H), 7.59(d, 2H), 7.64-7.69(m, 8H)

Molar extinction coefficient (365 nm); $1.2 \times 10^3$

Example A2

In a 100 mL four-necked flask equipped with a stirrer, a thermometer and a condenser, 6.9 g (0.02 mol) of bis(4-n-butoxyphenyl)sulfoxide, 2.0 g (0.01 mol) of 2,2'-dithienyl sulfide and 10.2 g (0.1 mol) of acetic anhydride were charged and 7.7 g (0.08 mol) of methanesulfonic acid was added dropwise over 1 hour while maintaining the inner temperature at 0 to 10° C. After completion of the dropwise addition, stirring was conducted for 2 hours while maintaining at the same temperature to obtain a reaction solution as a condensation reaction product.

In a 200 mL four-necked flask equipped with a stirrer, a thermometer and a condenser, 3.7 g (0.02 mol) of potassium hexafluorophosphate, 40 g of water and 30 g of monochlorobenzene were charged and the entire amount of the reaction solution was added dropwise over 30 minutes while maintaining the inner temperature at 30 to 50° C. After stirring at 40 to 50° C. for 30 minutes, the monochlorobenzene layer was separated and monochlorobenzene was distilled off to obtain 11.5 g of a brown concentrate.

This concentrate was purified by silica gel column chromatography to obtain 9.0 g (0.008 mol) of (thiodi-5,2-thienylene)bis[bis(4-n-butoxyphenyl)sulfonium]bishexafluorophosphate as a pale yellow solid. As a result of the measurement by high performance liquid chromatograph, purity of the resultant (thiodi-5,2-thienylene)bis[bis(4-n-butoxyphenyl)sulfonium]bishexafluorophosphate was 98.5%. Also, the yield to 2,2'-dithienyl sulfide was 78%.

It was confirmed by analytical results shown below that the resultant pale yellow solid is (thiodi-5,2-thienylene)bis[bis(4-n-butoxyphenyl)sulfonium]bishexafluorophosphate in which all $R^{1a}$, $R^{2a}$, $R^{3a}$ and $R^{4a}$ in the formula (A1) are 4-n-butoxyphenyl groups and $X^-$ is a hexafluorophosphoric acid ion. The molar extinction coefficient was determined by measuring using a spectrophotometer for ultraviolet and visible region (manufactured by Shimadzu Corporation under the trade name of UV-2500(PC)S).

Elemental analysis: C; 50.1%, H; 4.8%, F; 20.1%, O; 5.6%, S; 14.2% (theoretical value: C; 50.25%, H; 4.92%, F; 19.87%, O; 5.58%, S; 13.98%)

$^1$H-Nuclear magnetic resonance spectrum (400 MHz, $CD_2Cl_2$) δ (ppm): 0.98(t, 12H), 1.45-1.56(m, 8H), 1.76-1.85 (m, 8H), 4.08(t, 8H), 7.16-7.22(m, 8H), 7.44(d, 2H), 7.58(d, 2H), 7.63-7.68(m, 8H)

Molar extinction coefficient (365 nm); $1.1 \times 10^3$

Example A3

In a 100 mL four-necked flask equipped with a stirrer, a thermometer and a condenser, 6.4 g (0.02 mol) of bis(4-isopropoxyphenyl)sulfoxide, 2.0 g (0.01 mol) of 2,2'-dithienyl sulfide and 10.2 g (0.1 mol) of acetic anhydride were charged and 7.7 g (0.08 mol) of methanesulfonic acid was added dropwise over 1 hour while maintaining the inner temperature at 0 to 10° C. After completion of the dropwise addition, stirring was conducted for 2 hours while maintaining at the same temperature to obtain a reaction solution as a condensation reaction product.

In a 200 mL four-necked flask equipped with a stirrer, a thermometer and a condenser, 3.7 g (0.02 mol) of potassium hexafluorophosphate, 40 g of water and 30 g of monochlorobenzene were charged and the entire amount of the reaction solution was added dropwise over 30 minutes while maintaining the inner temperature at 30 to 50° C. After stirring at 40 to 50° C. for 30 minutes, the monochlorobenzene layer was separated and monochlorobenzene was distilled off to obtain 12.0 g of a brown concentrate.

This concentrate was purified by silica gel column chromatography to obtain 8.9 g (0.008 mol) of (thiodi-5,2-thienylene)bis[bis(4-isopropoxyphenyl)sulfonium]bishexafluorophosphate as a pale yellow solid. As a result of the measurement by high performance liquid chromatograph, purity of the resultant (thiodi-5,2-thienylene)bis[bis(4-isopropoxyphenyl)sulfonium]bishexafluorophosphate was 98.8%. Also, the yield to 2,2'-dithienyl sulfide was 82%.

It was confirmed by analytical results shown below that the resultant pale yellow solid is (thiodi-5,2-thienylene)bis[bis(4-isopropoxyphenyl)sulfonium]bishexafluorophosphate in which all $R^{1a}$, $R^{2a}$, $R^{3a}$ and $R^{4a}$ in the formula (A1) are 4-isopropoxyphenyl groups and $X^-$ is a hexafluorophosphoric acid ion. The molar extinction coefficient was determined by measuring using a spectrophotometer for ultraviolet and visible region (manufactured by Shimadzu Corporation under the trade name of UV-2500(PC)S).

Elemental analysis: C; 48.6%, H; 4.3%, F; 21.0%, O; 5.8%, S; 14.9% (theoretical value: C; 48.43%, H; 4.43%, F; 20.89%, O; 5.87%, S; 14.69%)

$^1$H-Nuclear magnetic resonance spectrum (400 MHz, $CD_2Cl_2$) δ (ppm): 1.38(d, 24H), 4.65-4.75(m, 4H), 7.12-7.20 (m, 8H), 7.44(d, 2H), 7.56(d, 2H), 7.62-7.67(m, 8H)

Molar extinction coefficient (365 nm); $0.6 \times 10^3$

Example A4

In a 100 mL four-necked flask equipped with a stirrer, a thermometer and a condenser, 4.6 g (0.02 mol) of bis(4-methylphenyl)sulfoxide, 2.0 g (0.01 mol) of 2,2'-dithienyl sulfide and 10.2 g (0.1 mol) of acetic anhydride were charged and 7.7 g (0.08 mol) of methanesulfonic acid was added dropwise over 1 hour while maintaining the inner temperature at 0 to 10° C. After completion of the dropwise addition, stirring was conducted for 2 hours while maintaining at the same temperature to obtain a reaction solution as a condensation reaction product.

In a 200 mL four-necked flask equipped with a stirrer, a thermometer and a condenser, 3.7 g (0.02 mol) of potassium hexafluorophosphate, 40 g of water and 30 g of monochlorobenzene were charged and the entire amount of the reaction solution was added dropwise over 30 minutes while maintaining the inner temperature at 30 to 50° C. After stirring at 40 to 50° C. for 30 minutes, the monochlorobenzene layer was separated and monochlorobenzene was distilled off to obtain 8.5 g of a brown concentrate.

This concentrate was purified by silica gel column chromatography to obtain 6.4 g (0.007 mol) of (thiodi-5,2-thienylene)bis[bis(4-methylphenyl)sulfonium]bishexafluorophosphate as a pale yellow solid. As a result of the measurement by high performance liquid chromatograph, purity of the resultant (thiodi-5,2-thienylene)bis[bis(4-methylphenyl)sulfonium]bishexafluorophosphate was 98.3%. Also, the yield to 2,2'-dithienyl sulfide was 70%.

It was confirmed by analytical results shown below that the resultant pale yellow solid is (thiodi-5,2-thienylene)bis[bis(4-methylphenyl)sulfonium]bishexafluorophosphate in which all $R^{1a}$, $R^{2a}$, $R^{3a}$ and $R^{4a}$ in the formula (A1) are 4-methylphenyl groups and X⁻ is a hexafluorophosphoric acid ion. The molar extinction coefficient was determined by measuring using a spectrophotometer for ultraviolet and visible region (manufactured by Shimadzu Corporation under the trade name of UV-2500(PC)S).

Elemental analysis: C; 47.1%, H; 3.4%, F; 25.1%, S; 17.6% (theoretical value: C; 47.26%, H; 3.53%, F; 24.92%, S; 17.52%)

$^1$H-Nuclear magnetic resonance spectrum (400 MHz, $CD_2Cl_2$) δ (ppm): 2.50(s, 12H), 7.46-7.48(m, 2H), 7.52-7.56 (m, 8H), 7.57-7.62(m, 8H), 7.69(d, 2H)

Molar extinction coefficient (365 nm); $1.5×10^3$

Example A5

In a 100 mL four-necked flask equipped with a stirrer, a thermometer and a condenser, 5.2 g (0.02 mol) of bis(4-methoxyphenyl)sulfoxide, 2.0 g (0.01 mol) of 2,2'-dithienyl sulfide and 10.2 g (0.1 mol) of acetic anhydride were charged and 7.7 g (0.08 mol) of methanesulfonic acid was added dropwise over 1 hour while maintaining the inner temperature at 0 to 10° C. After completion of the dropwise addition, stirring was conducted for 2 hours while maintaining at the same temperature to obtain a reaction solution as a condensation reaction product.

In a 300 mL four-necked flask equipped with a stirrer, a thermometer and a condenser, 18.8 g (0.02 mol) of lithium tetrakis(pentafluorophenyl)borate (73 wt %-diethylether complex), 100 g of water and 50 g of monochlorobenzene were charged and the entire amount of the reaction solution was added dropwise over 30 minutes while maintaining the inner temperature at 30 to 50° C. After stirring at 40 to 50° C. for 30 minutes, the monochlorobenzene layer was separated and monochlorobenzene was distilled off to obtain 21.0 g of a brown concentrate.

This concentrate was purified by silica gel column chromatography to obtain 15.3 g (0.007 mol) of (thiodi-5,2-thienylene)bis[bis(4-methoxyphenyl)sulfonium]bis[tetrakis (pentafluorophenyl)borate] as a pale yellow solid. As a result of the measurement by high performance liquid chromatograph, purity of the resultant (thiodi-5,2-thienylene)bis[bis (4-methoxyphenyl)sulfonium]bis[tetrakis(pentafluorophenyl)borate] was 98.5%. Also, the yield to 2,2'-dithienyl sulfide was 75%.

It was confirmed by analytical results shown below that the resultant pale yellow solid is (thiodi-5,2-thienylene)bis[bis (4-methoxyphenyl)sulfonium]bis[tetrakis(pentafluorophenyl)borate] in which all $R^{1a}$, $R^{2a}$, $R^{3a}$ and $R^{4a}$ in the formula (A1) are 4-methoxyphenyl groups and X⁻ is a tetrakis(pentafluorophenyl)boric acid ion. The molar extinction coefficient was determined by measuring using a spectrophotometer for ultraviolet and visible region (manufactured by Shimadzu Corporation under the trade name of UV-2500(PC) S).

Elemental analysis: C; 49.4%, H; 1.5%, F; 37.1%, O; 3.0%, S; 8.0% (theoretical value: C; 49.29%, H; 1.58%, F; 37.12%, O; 3.13%, S; 7.83%)

$^1$H-Nuclear magnetic resonance spectrum (400 MHz, $CD_2Cl_2$) δ (ppm): 3.90(s, 12H), 7.11-7.16(m, 8H), 7.33(d, 2H), 7.42(d, 2H), 7.48-7.53(m, 8H)

Molar extinction coefficient (365 nm); $0.9×10^3$

Example A6

In a 5 ml vessel made of glass, 50 mg of (thiodi-5,2-thienylene)bis[bis(4-methoxyphenyl)sulfonium]bishexafluorophosphate obtained in Example A1 as a photoacid generator, 1 g of 3,4-epoxycyclohexylmethyl-3,4-epoxycyclohexane carboxylate and 1 g of bis(3-ethyl-3-oxetanylmethyl)ether, which are cation polymerizable compounds, as acid reactive compounds, and 0.45 g of propylene carbonate as a solvent were charged, followed by mixing and stirring at 25° C. for 30 minutes to obtain a photoreactive composition.

Example A7

In the same manner as in Example A6, except that 50 mg of (thiodi-5,2-thienylene)bis[bis(4-n-butoxyphenyl)sulfonium] bishexafluorophosphate obtained in Example A2 was used in place of 50 mg of (thiodi-5,2-thienylene)bis[bis(4-methoxyphenyl)sulfonium]bishexafluorophosphate in Example A6, a photoreactive composition was obtained.

Example A8

In the same manner as in Example A6, except that 50 mg of (thiodi-5,2-thienylene)bis[bis(4-isopropoxyphenyl)sulfonium]bishexafluorophosphate obtained in Example A3 was used in place of 50 mg of (thiodi-5,2-thienylene)bis[bis(4-methoxyphenyl)sulfonium]bishexafluorophosphate in Example A6, a photoreactive composition was obtained.

Example A9

In the same manner as in Example A6, except that 50 mg of (thiodi-5,2-thienylene)bis[bis(4-methylphenyl)sulfonium] bishexafluorophosphate obtained in Example A4 was used in place of 50 mg of (thiodi-5,2-thienylene)bis[bis(4-methoxyphenyl)sulfonium]bishexafluorophosphate in Example A6, a photoreactive composition was obtained.

Example A10

In the same manner as in Example A6, except that 50 mg of (thiodi-5,2-thienylene)bis[bis(4-methoxyphenyl)sulfonium] bis[tetrakis(pentafluorophenyl)borate] obtained in Example A5 was used in place of 50 mg of (thiodi-5,2-thienylene)bis [bis(4-methoxyphenyl)sulfonium]bishexafluorophosphate in Example A6, a photoreactive composition was obtained.

Comparative Example A1

In a 100 mL four-necked flask equipped with a stirrer, a thermometer and a condenser, 3.5 g (0.015 mol) of bis(4-methylphenyl)sulfoxide, 2.5 g (0.015 mol) of 2,2'-bithiophene and 7.7 g (0.075 mol) of acetic anhydride were charged and 5.8 g (0.06 mol) of methanesulfonic acid was added dropwise over 1 hour while maintaining the inner temperature at 0 to 10° C. After completion of the dropwise addition, stirring was conducted at the same temperature for 2 hours and also stirring was conducted at 20 to 30° C. for 2 hours to obtain a reaction solution of a condensation reaction product.

In a 200 mL four-necked flask equipped with a stirrer, a thermometer and a condenser, 2.8 g (0.015 mol) of potassium hexafluorophosphate, 40 g of water and 30 g of monochlorobenzene were charged and the entire amount of the reaction solution was added dropwise over 30 minutes while maintaining the inner temperature at 30 to 50° C. After stirring at 40 to 50° C. for 30 minutes, the monochlorobenzene layer was separated and monochlorobenzene was distilled off to obtain 7.5 g of a green concentrate.

This concentrate was purified by silica gel column chromatography to obtain 5.4 g of bis(4-methylphenyl)-5-(2,2'- bithienyl)sulfonium hexafluorophosphate, which is the aromatic sulfonium salt described in Patent Document 3, as a pale yellow solid. As a result of the measurement by high performance liquid chromatograph, purity of the resultant bis(4-methylphenyl)-5-(2,2'-bithienyl)sulfonium hexafluorophosphate was 98.9%. A molar extinction coefficient was determined by measuring using a spectrophotometer for ultraviolet and visible region (manufactured by Shimadzu Corporation under the trade name of UV-2500(PC)S).

Molar extinction coefficient (365 nm); $1.2 \times 10^4$

Comparative Example A2

In the same manner as in Example A6, except that 50 mg of bis(4-methylphenyl)-5-(2,2'-bithienyl)sulfonium hexafluorophosphate obtained in Comparative Example A1 was used in place of 50 mg of (thiodi-5,2-thienylene)bis[bis(4-methoxyphenyl)sulfonium]bishexafluorophosphate in Example A6, a photoreactive composition was obtained.

Comparative Example A3

In the same manner as in Example A6, except that 50 mg of triphenylsulfonium hexafluorophosphate, which had hitherto been used widely as a photoacid generator, was used in place of 50 mg of (thiodi-5,2-thienylene)bis[bis(4-methoxyphenyl)sulfonium]bishexafluorophosphate in Example A6, a photoreactive composition was obtained.

Evaluation of Photoreactivity

With respect to each of the photoreactive compositions obtained in Examples A6 to A10 and Comparative Examples A2 to A3, photoreactivity was evaluated.

Regarding the method for evaluation, a heat generation initiation time and a calorific value after light irradiation were measured using a photochemical reaction calorimeter (manufactured by SII NanoTechnology Inc. under the trade name of PDC121). Since all photoreactive compositions thus evaluated contain a cation polymerizable compound as an acid reactive compound, the cure state after the measurement was also observed.

Regarding the method for measurement of the reaction calorific value, a predetermined amount of a photoreactive composition was charged in a predetermined open cup made of aluminum and irradiated with light each having a wavelength of 365 nm (i-line) and 405 nm (h-line) at a light intensity of 10 mW/cm$^2$ for 2 minutes, and then the reaction calorific value was measured. The amount of each photoreactive composition charged was 3 mg.

The evaluation results are shown in Table 1.

TABLE 1

| | Wavelength (nm) | Heat generation initiation time (minutes) | Calorific value (mJ/mg) | Cure state |
|---|---|---|---|---|
| Example A6 | 365 | 0.02 | 370 | Cured |
| | 405 | 0.04 | 320 | Cured |
| Example A7 | 365 | 0.03 | 380 | Cured |
| | 405 | 0.04 | 320 | Cured |
| Example A8 | 365 | 0.02 | 380 | Cured |
| | 405 | 0.05 | 300 | Cured |
| Example A9 | 365 | 0.03 | 350 | Cured |
| | 405 | 0.06 | 290 | Cured |
| Example A10 | 365 | 0.03 | 370 | Cured |
| | 405 | 0.04 | 330 | Cured |
| Comparative Example A2 | 365 | 1.0 | 40 | Tar-like state |
| | 405 | 1.5 | 10 | Not cured, liquid |
| Comparative Example A3 | 365 | — | 0 | Not cured, liquid |
| | 405 | — | 0 | Not cured, liquid |

As is apparent from the results shown in Table 1, in the photoreactive compositions obtained in Examples A6 to A10, heat generation is recognized within a very short time after irradiation with light in the near ultraviolet range of 365 nm and 405 nm and also a calorific value is large. It was also observed that all photoreactive compositions obtained in Examples A6 to A10 were cured after the measurement.

Therefore, it can be said that the photoreactive compositions obtained in Examples A6 to A10 are photoreactive compositions in which the reaction time by irradiation with light in the near ultraviolet range is very short, and that the dithienyl sulfide disulfonium salt according to the present invention used in the photoreactive composition is a photoacid generator which shows very high sensitivity in the near ultraviolet range and can remarkably increase the reaction rate of the photoreactive composition.

Example B1

In a 100 mL four-necked flask equipped with a stirrer, a thermometer and a condenser, 2.6 g (0.01 mol) of bis(4-methoxyphenyl)sulfoxide, 2.0 g (0.01 mol) of 2,2'-dithienyl sulfide and 5.1 g (0.05 mol) of acetic anhydride were charged and 3.8 g (0.04 mol) of methanesulfonic acid was added dropwise over 30 minutes while maintaining the inner temperature at 0 to 10° C. After completion of the dropwise addition, stirring was conducted for 2 hours while maintaining at the same temperature to obtain a reaction solution as a condensation reaction product.

In a 200 mL four-necked flask equipped with a stirrer, a thermometer and a condenser, 1.8 g (0.01 mol) of potassium hexafluorophosphate, 20 g of water and 20 g of monochlorobenzene were charged and the entire amount of the reaction solution was added dropwise over 30 minutes while maintaining the inner temperature at 30 to 50° C. After stirring at 40 to 50° C. for 30 minutes, the monochlorobenzene layer was separated and monochlorobenzene was distilled off to obtain 5.9 g of a brown concentrate.

This concentrate was purified by silica gel column chromatography to obtain 4.2 g (0.007 mol) of bis(4-methoxyphenyl)[5-(thiophen-2-ylthio)-thiophen-2-yl]sulfonium hexafluorophosphate as a pale yellow tar-like substance. As a result of the measurement by high performance liquid chromatograph, purity of the resultant bis(4-methoxyphenyl)[5-(thiophen-2-ylthio)-thiophen-2-yl]sulfonium hexafluorophosphate was 98.7%. Also, the yield to 2,2'-dithienyl sulfide was 71%.

It was confirmed by analytical results shown below that the resultant pale yellow tar-like substance is bis(4-methoxyphenyl)[5-(thiophen-2-ylthio)-thiophen-2-yl]sulfonium hexafluorophosphate in which all $R^{1b}$ and $R^{2b}$ in the formula (B1) are 4-methoxyphenyl groups, all $R^{3b}$ to $R^{5b}$ are hydrogen atoms, and $X^-$ is a hexafluorophosphoric acid ion. The molar extinction coefficient was determined by measuring using a spectrophotometer for ultraviolet and visible region (manufactured by Shimadzu Corporation under the trade name of UV-2500(PC)S).

Elemental analysis: C; 44.8%, H; 3.1%, F; 19.6%, O; 5.4%, S; 21.7% (theoretical value: C; 44.89%, H; 3.25%, F; 19.37%, O; 5.44%, S; 21.79%)

$^1$H-Nuclear magnetic resonance spectrum (400 MHz, CD$_2$Cl$_2$) δ (ppm): 3.92(s, 6H), 7.10-7.14(m, 1H), 7.16-7.21 (m, 5H), 7.40-7.42(m, 1H), 7.54-7.59(m, 4H), 7.60-7.63(m, 2H)

Maximum absorption wavelength: 315.5 nm
Molar extinction coefficient (365 nm): 0.2×10$^3$ Example B2

In a 100 mL four-necked flask equipped with a stirrer, a thermometer and a condenser, 3.5 g (0.01 mol) of bis(4-n-butoxyphenyl)sulfoxide, 2.0 g (0.01 mol) of 2,2'-dithienyl sulfide and 5.1 g (0.05 mol) of acetic anhydride were charged and 3.8 g (0.04 mol) of methanesulfonic acid was added dropwise over 30 minutes while maintaining the inner temperature at 0 to 10° C. After completion of the dropwise addition, stirring was conducted for 2 hours while maintaining at the same temperature to obtain a reaction solution as a condensation reaction product.

In a 200 mL four-necked flask equipped with a stirrer, a thermometer and a condenser, 1.8 g (0.01 mol) of potassium hexafluorophosphate, 20 g of water and 20 g of monochlorobenzene were charged and the entire amount of the reaction solution was added dropwise over 30 minutes while maintaining the inner temperature at 30 to 50° C. After stirring at 40 to 50° C. for 30 minutes, the monochlorobenzene layer was separated and monochlorobenzene was distilled off to obtain 7.3 g of a yellow concentrate.

This concentrate was purified by silica gel column chromatography to obtain 4.4 g (0.007 mol) of bis(4-n-butoxyphenyl)[5-(thiophen-2-ylthio)-thiophen-2-yl]sulfonium hexafluorophosphate as a pale yellow tar-like substance. As a result of the measurement by high performance liquid chromatograph, purity of the resultant bis(4-n-butoxyphenyl)[5-(thiophen-2-ylthio)-thiophen-2-yl]sulfonium hexafluorophosphate was 98.7%. Also, the yield to 2,2'-dithienyl sulfide was 66%.

It was confirmed by analytical results shown below that the resultant pale yellow tar-like substance is bis(4-n-butoxyphenyl)[5-(thiophen-2-ylthio)-thiophen-2-yl]sulfonium hexafluorophosphate in which all $R^{1b}$ and $R^{2b}$ in the formula (B1) are 4-n-butoxyphenyl groups, all $R^{3b}$ to $R^{5b}$ are hydrogen atoms, and X$^-$ is a hexafluorophosphoric acid ion. The molar extinction coefficient was determined by measuring using a spectrophotometer for ultraviolet and visible region (manufactured by Shimadzu Corporation under the trade name of UV-2500(PC)S).

Elemental analysis: C; 50.0%, H; 4.6%, F; 17.1%, O; 4.6%, S; 19.3% (theoretical value: C; 49.99%, H; 4.64%, F; 16.94%, O; 4.76%, S; 19.06%)

$^1$H-Nuclear magnetic resonance spectrum (400 MHz, CD$_2$Cl$_2$) δ (ppm): 0.98(t, 6H), 1.44-1.57(m, 4H), 1.76-1.85 (m, 4H), 4.07(t, 4H), 7.10-7.20(m, 6H), 7.40-7.42(m, 1H), 7.52-7.57(m, 4H), 7.59-7.63(m, 2H)

Molar extinction coefficient (365 nm): 0.2×10$^3$

Example B3

In a 100 mL four-necked flask equipped with a stirrer, a thermometer and a condenser, 3.2 g (0.01 mol) of bis(4-isopropoxyphenyl)sulfoxide, 2.0 g (0.01 mol) of 2,2'-dithienyl sulfide and 5.1 g (0.05 mol) of acetic anhydride were charged and 3.8 g (0.04 mol) of methanesulfonic acid was added dropwise over 30 minutes while maintaining the inner temperature at 0 to 10° C. After completion of the dropwise addition, stirring was conducted for 2 hours while maintaining at the same temperature to obtain a reaction solution as a condensation reaction product.

In a 200 mL four-necked flask equipped with a stirrer, a thermometer and a condenser, 1.8 g (0.01 mol) of potassium hexafluorophosphate, 20 g of water and 20 g of monochlorobenzene were charged and the entire amount of the reaction solution was added dropwise over 30 minutes while maintaining the inner temperature at 30 to 50° C. After stirring at 40 to 50° C. for 30 minutes, the monochlorobenzene layer was separated and monochlorobenzene was distilled off to obtain 6.6 g of a brown concentrate.

This concentrate was purified by silica gel column chromatography to obtain 5.2 g (0.008 mol) of bis(4-isopropoxyphenyl)[5-(thiophen-2-ylthio)-thiophen-2-yl]sulfonium hexafluorophosphate as a pale yellow solid. As a result of the measurement by high performance liquid chromatograph, purity of the resultant bis(4-isopropoxyphenyl)[5-(thiophen-2-ylthio)-thiophen-2-yl]sulfonium hexafluorophosphate was 98.6%. Also, the yield to 2,2'-dithienyl sulfide was 80%.

It was confirmed by analytical results shown below that the resultant pale yellow solid is bis(4-isopropoxyphenyl)[5-(thiophen-2-ylthio)-thiophen-2-yl]sulfonium hexafluorophosphate in which all $R^{1b}$ and $R^{2b}$ in the formula (B1) are 4-isopropoxyphenyl groups, all $R^{3b}$ to $R^{5b}$ are hydrogen atoms, and X$^-$ is a hexafluorophosphoric acid ion. The molar extinction coefficient was determined by measuring using a spectrophotometer for ultraviolet and visible region (manufactured by Shimadzu Corporation under the trade name of UV-2500(PC)S).

Elemental analysis: C; 48.3%, H; 4.2%, F; 17.6%, O; 5.2%, S; 20.1% (theoretical value: C; 48.44%, H; 4.22%, F; 17.68%, O; 4.96%, S; 19.89%)

$^1$H-Nuclear magnetic resonance spectrum (400 MHz, CD$_2$Cl$_2$) δ (ppm): 1.38(d, 12H), 4.63-4.74(m, 2H), 7.10-7.16 (m, 5H), 7.16-7.18(m, 1H), 7.40-7.42(m, 1H), 7.51-7.56(m, 4H), 7.58-7.60(m, 1H), 7.60-7.62(m, 1H)

Molar extinction coefficient (365 nm): 0.2×10$^3$

Example B4

In a 100 mL four-necked flask equipped with a stirrer, a thermometer and a condenser, 2.6 g (0.01 mol) of bis(4-methoxyphenyl)sulfoxide, 2.0 g (0.01 mol) of 2,2'-dithienyl sulfide and 5.1 g (0.05 mol) of acetic anhydride were charged and 3.8 g (0.04 mol) of methanesulfonic acid was added dropwise over 30 minutes while maintaining the inner temperature at 0 to 10° C. After completion of the dropwise addition, stirring was conducted for 2 hours while maintaining at the same temperature to obtain a reaction solution as a condensation reaction product.

In a 200 mL four-necked flask equipped with a stirrer, a thermometer and a condenser, 9.4 g (0.01 mol) of lithium tetrakis(pentafluorophenyl)borate (73 wt %-diethylether complex), 50 g of water and 30 g of monochlorobenzene were charged and the entire amount of the reaction solution was added dropwise over 30 minutes while maintaining the inner temperature at 30 to 50° C. After stirring at 40 to 50° C. for 30 minutes, the monochlorobenzene layer was separated and monochlorobenzene was distilled off to obtain 10.9 g of a brown concentrate.

This concentrate was purified by silica gel column chromatography to obtain 7.6 g (0.007 mol) of bis(4-methoxyphenyl)[5-(thiophen-2-ylthio)-thiophen-2-yl]sulfonium tetrakis(pentafluorophenyl)borate as a pale yellow solid. As a result of the measurement by high performance liquid chromatograph, purity of the resultant bis(4-methoxyphenyl)[5-(thiophen-2-ylthio)-thiophen-2-yl]sulfonium tetrakis(pentafluorophenyl)borate was 98.8%. Also, the yield to 2,2'-dithienyl sulfide was 68%.

It was confirmed by analytical results shown below that the resultant pale yellow solid is bis(4-methoxyphenyl)[5-(thiophen-2-ylthio)-thiophen-2-yl]sulfonium tetrakis(pentafluorophenyl)borate in which all $R^{1b}$ and $R^{2b}$ in the formula (B1) are 4-methoxyphenyl groups, all $R^{3b}$ to $R^{5b}$ are hydrogen atoms, and $X^-$ is a tetrakis(pentafluorophenyl)boric acid ion. The molar extinction coefficient was determined by measuring using a spectrophotometer for ultraviolet and visible region (manufactured by Shimadzu Corporation under the trade name of UV-2500(PC)S).

Elemental analysis: C; 49.3%, H; 1.7%, F; 33.6%, O; 2.9%, S; 11.3% (theoretical value: C; 49.21%, H; 1.71%, F; 33.84%, O; 2.85%, S; 11.42%)

$^1$H-Nuclear magnetic resonance spectrum (400 MHz, $CD_2Cl_2$) δ (ppm): 3.90(s, 6H), 7.10-7.13(m, 1H), 7.13-7.18 (m, 5H), 7.39-7.42(m, 1H), 7.46-7.51(m, 5H), 7.60-7.62(m, 1H)

Molar extinction coefficient (365 nm): $0.3 \times 10^2$

Example B5

In a 5 ml vessel made of glass, 50 mg of bis(4-methoxyphenyl)[5-(thiophen-2-ylthio)-thiophen-2-yl]sulfonium hexafluorophosphate obtained in Example B1 as a photoacid generator, 1 g of 3,4-epoxycyclohexylmethyl-3,4-epoxycyclohexane carboxylate and 1 g of bis(3-ethyl-3-oxetanylmethyl)ether, which are cation polymerizable compounds, as acid reactive compounds, and 0.45 g of propylene carbonate as a solvent were charged, followed by mixing and stirring at 25° C. for 30 minutes to obtain a photoreactive composition.

Example B6

In the same manner as in Example B5, except that 50 mg of bis(4-n-butoxyphenyl)[5-(thiophen-2-ylthio)-thiophen-2-yl]sulfonium hexafluorophosphate obtained in Example B2 was used in place of 50 mg of bis(4-methoxyphenyl)[5-(thiophen-2-ylthio)-thiophen-2-yl]sulfonium hexafluorophosphate in Example B5, a photoreactive composition was obtained.

Example B7

In the same manner as in Example B5, except that 50 mg of bis(4-isopropoxyphenyl)[5-(thiophen-2-ylthio)-thiophen-2-yl]sulfonium hexafluorophosphate obtained in Example B3 was used in place of 50 mg of bis(4-methoxyphenyl)[5-(thiophen-2-ylthio)-thiophen-2-yl]sulfonium hexafluorophosphate in Example B5, a photoreactive composition was obtained.

Example B8

In the same manner as in Example B5, except that 50 mg of bis(4-methoxyphenyl)[5-(thiophen-2-ylthio)-thiophen-2-yl]sulfonium tetrakis(pentafluorophenyl)borate obtained in Example B4 was used in place of 50 mg of bis(4-methoxyphenyl)[5-(thiophen-2-ylthio)-thiophen-2-yl]sulfonium hexafluorophosphate in Example B5, a photoreactive composition was obtained.

Comparative Example B1

In a 100 mL four-necked flask equipped with a stirrer, a thermometer and a condenser, 3.5 g (0.015 mol) of bis(4-methylphenyl)sulfoxide, 2.5 g (0.015 mol) of 2,2'-bithiophene and 7.7 g (0.075 mol) of acetic anhydride were charged and 5.8 g (0.06 mol) of methanesulfonic acid was added dropwise over 1 hour while maintaining the inner temperature at 0 to 10° C. After completion of the dropwise addition, stirring was conducted for 2 hours while maintaining at the same temperature and also stirring was conducted at 20 to 30° C. for 2 hours to obtain a reaction solution of a condensation reaction product.

In a 200 mL four-necked flask equipped with a stirrer, a thermometer and a condenser, 2.8 g (0.015 mol) of potassium hexafluorophosphate, 40 g of water and 30 g of monochlorobenzene were charged and the entire amount of the reaction solution was added dropwise over 30 minutes while maintaining the inner temperature at 30 to 50° C. After stirring at 40 to 50° C. for 30 minutes, the monochlorobenzene layer was separated and monochlorobenzene was distilled off to obtain 7.5 g of a green concentrate.

This concentrate was purified by silica gel column chromatography to obtain 5.4 g of bis(4-methylphenyl)-5-(2,2'-bithienyl)sulfonium hexafluorophosphate, which is the aromatic sulfonium salt described in Patent Document 3, as a pale yellow solid. As a result of the measurement by high performance liquid chromatograph, purity of the resultant bis(4-methylphenyl)-5-(2,2'-bithienyl)sulfonium hexafluorophosphate was 98.9%. A molar extinction coefficient was determined by measuring using a spectrophotometer for ultraviolet and visible region (manufactured by Shimadzu Corporation under the trade name of UV-2500(PC)S).

Molar extinction coefficient (365 nm): $1.2 \times 10^4$

Comparative Example B2

In the same manner as in Example B5, except that 50 mg of bis(4-methylphenyl)-5-(2,2'-bithienyl)sulfonium hexafluorophosphate obtained in Comparative Example B1 was used in place of 50 mg of bis(4-methoxyphenyl)[5-(thiophen-2-ylthio)-thiophen-2-yl]sulfonium hexafluorophosphate in Example B5, a photoreactive composition was obtained.

Comparative Example B3

In the same manner as in Example B5, except that 50 mg of triphenyl sulfonium hexafluorophosphate, which had hitherto been used widely as a photoacid generator, was used in place of 50 mg of bis(4-methoxyphenyl)[5-(thiophen-2-ylthio)-thiophen-2-yl]sulfonium hexafluorophosphate in Example B5, a photoreactive composition was obtained.

Evaluation of Photoreactivity

With respect to each of the photoreactive compositions obtained in Examples B5 to B8 and Comparative Examples B2 to B3, photoreactivity was evaluated.

Regarding the method for evaluation, a heat generation initiation time and a calorific value after light irradiation were measured using a photochemical reaction calorimeter (manufactured by SII NanoTechnology Inc. under the trade name of PDC121). Since all photoreactive compositions thus evaluated contain a cation polymerizable compound as an acid reactive compound, the cure state after the measurement was also observed.

Regarding the method for measurement of the reaction calorific value, a predetermined amount of a photoreactive composition was charged in a predetermined open cup made of aluminum and irradiated with light each having a wavelength of 365 nm (i-line) and 405 nm (h-line) at a light intensity of 10 mW/cm$^2$ for 2 minutes, and then the reaction calorific value was measured. The amount of each photoreactive composition charged was 3 mg.

The evaluation results are shown in Table 2.

TABLE 2

| | Wavelength (nm) | Heat generation initiation time (minutes) | Calorific value (mJ/mg) | Cure state |
|---|---|---|---|---|
| Example B5 | 365 | 0.04 | 355 | Cured |
| | 405 | 0.07 | 310 | Cured |
| Example B6 | 365 | 0.03 | 360 | Cured |
| | 405 | 0.06 | 290 | Cured |
| Example B7 | 365 | 0.03 | 365 | Cured |
| | 405 | 0.07 | 295 | Cured |
| Example B8 | 365 | 0.03 | 360 | Cured |
| | 405 | 0.07 | 320 | Cured |
| Comparative Example B2 | 365 | 1.0 | 40 | Tar-like state |
| | 405 | 1.5 | 10 | Not cured, liquid |
| Comparative Example B3 | 365 | — | 0 | Not cured, liquid |
| | 405 | — | 0 | Not cured, liquid |

As is apparent from the results shown in Table 2, in the photoreactive compositions obtained in Examples B5 to B8, heat generation is recognized within a very short time after irradiation with light in the near ultraviolet range of 365 nm and 405 nm and also a calorific value is large. It was also observed that all photoreactive compositions obtained in Examples B5 to B8 were cured after the measurement.

Therefore, it can be said that the photoreactive compositions obtained in Examples B5 to B8 are photoreactive compositions in which the reaction time by irradiation with light in the near ultraviolet range is very short, and that the dithienyl sulfide sulfonium salt according to the present invention used in the photoreactive composition is a photoacid generator which shows very high sensitivity in the near ultraviolet range and can remarkably increase the reaction rate of the photoreactive composition.

Example C1

In a 100 mL four-necked flask equipped with a stirrer, a thermometer and a condenser, 2.6 g (0.01 mol) of bis(4-methoxyphenyl)sulfoxide, 1.9 g (0.01 mol) of 2-(phenylthio)thiophene and 5.1 g (0.05 mol) of acetic anhydride were charged and 4.8 g (0.05 mol) of methanesulfonic acid was added dropwise over 1 hour while maintaining the inner temperature at 0 to 10° C. After completion of the dropwise addition, stirring was conducted for 3 hours while maintaining at the same temperature to obtain a reaction solution as a condensation reaction product.

In a 200 mL four-necked flask equipped with a stirrer, a thermometer and a condenser, 1.8 g (0.01 mol) of potassium hexafluorophosphate, 30 g of water and 20 g of monochlorobenzene were charged and the entire amount of the reaction solution was added dropwise over 30 minutes while maintaining the inner temperature at 30 to 50° C. After stirring at 40 to 50° C. for 30 minutes, the monochlorobenzene layer was separated and monochlorobenzene was distilled off to obtain 5.5 g of a brown concentrate.

This concentrate was purified by silica gel column chromatography to obtain 4.8 g (0.008 mol) of bis(4-methoxyphenyl)(5-phenylthio-thiophen-2-yl)sulfonium hexafluorophosphate as a pale yellow tar-like substance. As a result of the measurement by high performance liquid chromatograph, purity of the resultant bis(4-methoxyphenyl)(5-phenylthio-thiophen-2-yl)sulfonium hexafluorophosphate was 98.8%. Also, the yield to 2-(phenylthio)thiophene was 82%.

It was confirmed by analytical results shown below that the resultant pale yellow tar-like substance is bis(4-methoxyphenyl)(5-phenylthio-thiophen-2-yl)sulfonium hexafluorophosphate in which all $R^{1c}$ and $R^{2c}$ in the formula (C1) are 4-methoxyphenyl groups, all $R^{3c}$ to $R^{7c}$ are hydrogen atoms, and $X^-$ is a hexafluorophosphoric acid ion. The molar extinction coefficient was determined by measuring using a spectrophotometer for ultraviolet and visible region (manufactured by Shimadzu Corporation under the trade name of UV-2500(PC)S).

Elemental analysis: C; 49.3%, H; 3.7%, F; 19.7%, O; 5.4%, S; 16.8% (theoretical value: C; 49.48%, H; 3.63%, F; 19.57%, O; 5.49%, S; 16.51%)

$^1$H-Nuclear magnetic resonance spectrum (400 MHz, $CD_2Cl_2$) δ (ppm): 3.91(s, 6H), 7.16-7.22(m, 4H), 7.25(d, 1H), 7.39-7.44(m, 3H), 7.46-7.51(m, 2H), 7.56-7.62(m, 4H), 7.65(d, 1H)

Molar extinction coefficient (365 nm): $1.3 \times 10^3$

Example C2

In a 5 ml vessel made of glass, 50 mg of bis(4-methoxyphenyl)(5-phenylthio-thiophen-2-yl)sulfonium hexafluorophosphate obtained in Example C1 as a photoacid generator, 1 g of 3,4-epoxycyclohexylmethyl-3,4-epoxycyclohexane carboxylate and 1 g of bis(3-ethyl-3-oxetanylmethyl)ether, which are cation polymerizable compounds, as acid reactive compounds, and 0.45 g of propylene carbonate as a solvent were charged, followed by mixing and stirring at 25° C. for 30 minutes to obtain a photoreactive composition.

Comparative Example C1

In a 100 mL four-necked flask equipped with a stirrer, a thermometer and a condenser, 3.5 g (0.015 mol) of bis(4-methylphenyl)sulfoxide, 2.5 g (0.015 mol) of 2,2'-bithiophene and 7.7 g (0.075 mol) of acetic anhydride were charged and 5.8 g (0.06 mol) of methanesulfonic acid was added dropwise over 1 hour while maintaining the inner temperature at 0 to 10° C. After completion of the dropwise addition, stirring was conducted for 2 hours while maintaining at the same temperature and also stirring was conducted at 20 to 30° C. for 2 hours to obtain a reaction solution of a condensation reaction product.

In a 200 mL four-necked flask equipped with a stirrer, a thermometer and a condenser, 2.8 g (0.015 mol) of potassium hexafluorophosphate, 40 g of water and 30 g of monochlorobenzene were charged and the entire amount of the reaction solution was added dropwise over 30 minutes while maintaining the inner temperature at 30 to 50° C. After stirring at 40 to 50° C. for 30 minutes, the monochlorobenzene layer was separated and monochlorobenzene was distilled off to obtain 7.5 g of a green concentrate.

This concentrate was purified by silica gel column chromatography to obtain 5.4 g of bis(4-methylphenyl)-5-(2,2'-bithienyl)sulfonium hexafluorophosphate, which is the aromatic sulfonium salt described in Patent Document 3, as a pale yellow solid. As a result of the measurement by high performance liquid chromatograph, purity of the resultant bis(4-methylphenyl)-5-(2,2'-bithienyl)sulfonium hexafluorophosphate was 98.9%. A molar extinction coefficient was determined by measuring using a spectrophotometer for ultraviolet and visible region (manufactured by Shimadzu Corporation under the trade name of UV-2500(PC)S).

Molar extinction coefficient (365 nm): $1.2 \times 10^4$

Comparative Example C2

In the same manner as in Example C2, except that 50 mg of bis(4-methylphenyl)-5-(2,2'-bithienyl)sulfonium hexafluorophosphate obtained in Comparative Example C1 was used in place of 50 mg of bis(4-methoxyphenyl)(5-phenylthiothiophen-2-yl)sulfonium hexafluorophosphate in Example C2, a photoreactive composition was obtained.

Comparative Example C3

In the same manner as in Example C2, except that 50 mg of triphenylsulfonium hexafluorophosphate, which had hitherto been used widely as a photoacid generator, was used in place of 50 mg of bis(4-methoxyphenyl)(5-phenylthio-thiophen-2-yl)sulfonium hexafluorophosphate in Example C2, a photoreactive composition was obtained.

Evaluation of Photoreactivity

With respect to each of the photoreactive compositions obtained in Example C2 and Comparative Examples C2 to C3, photoreactivity was evaluated.

Regarding the method for evaluation, a heat generation initiation time and a calorific value after light irradiation were measured using a photochemical reaction calorimeter (manufactured by SII NanoTechnology Inc. under the trade name of PDC121). Since all photoreactive compositions thus evaluated contain a cation polymerizable compound as an acid reactive compound, the cure state after the measurement was also observed.

Regarding the method for measurement of the reaction calorific value, a predetermined amount of a photoreactive composition was charged in a predetermined open cup made of aluminum and irradiated with light each having a wavelength of 365 nm (i-line) and 405 nm (h-line) at a light intensity of 10 mW/cm² for 2 minutes, and then the reaction calorific value was measured. The amount of each photoreactive composition charged was 3 mg.

The evaluation results are shown in Table 3.

TABLE 3

| | Wavelength (nm) | Heat generation initiation time (minutes) | Calorific value (mJ/mg) | Cure state |
|---|---|---|---|---|
| Example C2 | 365 | 0.04 | 320 | Cured |
| | 405 | 0.10 | 290 | Cured |
| Comparative Example C2 | 365 | 1.0 | 40 | Tar-like state |
| | 405 | 1.5 | 10 | Not cured, liquid |
| Comparative Example C3 | 365 | — | 0 | Not cured, liquid |
| | 405 | — | 0 | Not cured, liquid |

As is apparent from the results shown in Table 3, in the photoreactive composition obtained in Example C2, heat generation is recognized within a very short time after irradiation with light in the near ultraviolet range of 365 nm and 405 nm and also a calorific value is large. It was also observed that the photoreactive composition obtained in Example C2 cured after the measurement.

Therefore, it can be said that the photoreactive composition obtained in Example C2 is a photoreactive composition in which the reaction time by irradiation with light in the near ultraviolet range is very short, and that the phenylthiothiophene sulfonium salt according to the present invention used in the photoreactive composition is a photoacid generator which shows very high sensitivity in the near ultraviolet range and can remarkably increase the reaction rate of the photoreactive composition.

The invention claimed is:

1. A dithienyl sulfide disulfonium salt represented by the formula (A1):

[Chemical Formula 1]

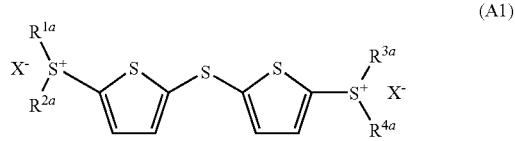

wherein $R^{1a}$ to $R^{4a}$ each independently represents an optionally substituted monocyclic carbon ring group, an optionally substituted condensed polycyclic carbon ring group or an optionally substituted monocyclic heterocyclic group, and $X^-$ represents an inorganic acid ion or an organic acid ion.

2. A photoacid generator comprising the dithienyl sulfide disulfonium salt according to claim 1.

3. A photoreactive composition comprising the photoacid generator according to claim 2 and an acid reactive compound.

4. A dithienyl sulfide sulfonium salt represented by the formula (B1):

[Chemical Formula 2]

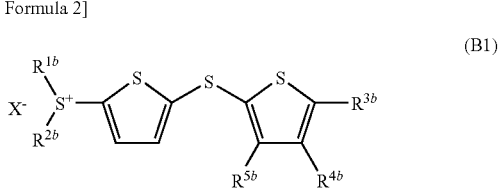

wherein $R^{1b}$ and $R^{2b}$ each independently represents an optionally substituted monocyclic carbon ring group, an optionally substituted condensed polycyclic carbon ring group or an optionally substituted monocyclic heterocyclic group, $R^{3b}$ to $R^{5b}$ each independently represents a hydrogen atom, an alkyl group having 1 to 10 carbon atoms, an alkoxy group having 1 to 4 carbon atoms, an acyl group or a hydroxyl group, and $X^-$ represents an inorganic acid ion or an organic acid ion.

5. A photoacid generator comprising the dithienyl sulfide sulfonium salt according to claim 4.

6. A photoreactive composition comprising the photoacid generator according to claim 5 and an acid reactive compound.

7. A phenylthiothiophene sulfonium salt represented by the formula (C1):

[Chemical Formula 3]

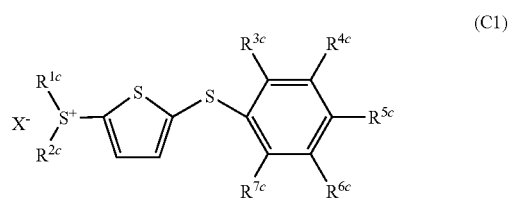

wherein $R^{1c}$ and $R^{2c}$ each independently represents an optionally substituted monocyclic carbon ring group, an optionally substituted condensed polycyclic carbon ring group or an optionally substituted monocyclic heterocyclic group, an $R^{3c}$ to $R^{7c}$ each independently represents a hydrogen atom, an alkyl group having 1 to 10 carbon atoms, an alkoxy group having 1 to 4 carbon atoms, an acyl group or a hydroxyl group, and $X^-$ represents an inorganic acid ion or an organic acid ion.

8. A photoacid generator comprising the phenylthiothiophene sulfonium salt according to claim 7.

9. A photoreactive composition comprising the photoacid generator according to claim 8 and an acid reactive compound.

* * * * *